United States Patent
Cole et al.

(10) Patent No.: US 9,480,496 B2
(45) Date of Patent: *Nov. 1, 2016

(54) FOLLICULAR DISSECTION DEVICE AND METHOD

(75) Inventors: John P. Cole, Alpharetta, GA (US); Tesfaye H. Gutema, Alpharetta, GA (US)

(73) Assignee: Cole Isolation Technique, LLC, Alpharetta, GA (US)

( * ) Notice: Subject to any disclaimer, the term of this patent is extended or adjusted under 35 U.S.C. 154(b) by 1139 days.

This patent is subject to a terminal disclaimer.

(21) Appl. No.: 11/508,669

(22) Filed: Aug. 22, 2006

(65) Prior Publication Data

US 2007/0293884 A9    Dec. 20, 2007

Related U.S. Application Data

(63) Continuation-in-part of application No. 11/325,388, filed on Jan. 3, 2006, now Pat. No. 8,753,354, which is a continuation-in-part of application No. 10/795,835, filed on Mar. 9, 2004, now Pat. No. 7,172,604.

(51) Int. Cl.
*A61B 17/34* (2006.01)
*A61B 17/322* (2006.01)
(Continued)

(52) U.S. Cl.
CPC ....... *A61B 17/322* (2013.01); *A61B 17/32053* (2013.01); *A61B 17/3403* (2013.01);
(Continued)

(58) Field of Classification Search
CPC ........... A61B 17/32053; A61B 17/3468; A61B 17/322; A61B 17/3403; A61B 17/34; A61B 17/3496; A61B 2017/00902; A61B 2017/3492; A61B 2017/00969; A61B 2017/00752; A61B 2019/306; A61B 2019/462; A61B 2090/036; A61B 2090/062
USPC ....... 606/133, 131, 187, 184, 185, 167, 170, 606/132, 32, 166, 186, 172; 600/566, 567; 604/173; 30/305; 623/15.11
See application file for complete search history.

(56) References Cited

U.S. PATENT DOCUMENTS 2,360,051 A    10/1944    Eweson
3,035,580 A     5/1962    Methodi
(Continued)

FOREIGN PATENT DOCUMENTS

FR    2744624 A      8/1997
WO    98/47434      10/1998
(Continued)

OTHER PUBLICATIONS

Response to Restriction Requirement filed Feb. 2, 2009 in related matter U.S. Appl. No. 11/558,338, 12 pages.
(Continued)

*Primary Examiner* — Melanie Tyson
*Assistant Examiner* — Tin Nguyen
(74) *Attorney, Agent, or Firm* — Berkeley Law & Technology Group, LLP

(57) ABSTRACT

Provided herein is an apparatus and method useful for surgical removal of mammalian tissue. In one or more implementations, a cylindrical punch having one or more cutting edges may be provided for surgically extracting one or more hair follicles during a follicular dissection procedure. In one or more implementations, one or more cutting edges may be located along an outside diameter of a cylindrical punch.

10 Claims, 26 Drawing Sheets

(51) Int. Cl.
*A61B 17/3205* (2006.01)
*A61B 17/00* (2006.01)

(52) U.S. Cl.
CPC ....... *A61B17/3468* (2013.01); *A61B 17/3496* (2013.01); *A61B 2017/00752* (2013.01); *A61B 2017/00902* (2013.01); *A61B 2017/00969* (2013.01); *A61B 2017/3492* (2013.01); *A61B 2090/036* (2016.02); *A61B 2090/062* (2016.02)

(56) References Cited

U.S. PATENT DOCUMENTS

| | | | |
|---|---|---|---|
| 3,913,566 | A | 10/1975 | Lacey |
| 3,990,453 | A * | 11/1976 | Douvas et al. ............... 606/107 |
| 3,998,230 | A | 12/1976 | Miller |
| 4,263,913 | A | 4/1981 | Malmin |
| 4,476,864 | A | 10/1984 | Tezel |
| 4,798,213 | A * | 1/1989 | Doppelt ........................ 600/567 |
| 4,873,991 | A | 10/1989 | Skinner |
| 4,994,028 | A * | 2/1991 | Leonard et al. ................ 604/60 |
| 5,269,316 | A | 12/1993 | Spitalny |
| 5,417,683 | A | 5/1995 | Shiao |
| 5,423,330 | A * | 6/1995 | Lee ............... 600/566 |
| 5,439,475 | A | 8/1995 | Bennett |
| 5,507,765 | A | 4/1996 | Mott |
| 5,578,054 | A | 11/1996 | Arnold |
| 5,613,978 | A | 3/1997 | Harding |
| 5,662,661 | A | 9/1997 | Boudjema |
| 5,676,680 | A * | 10/1997 | Lim ............................. 606/176 |
| 5,693,064 | A * | 12/1997 | Arnold ........................ 606/184 |
| 5,707,362 | A | 1/1998 | Yoon |
| 5,725,553 | A | 3/1998 | Moenning |
| 5,766,177 | A | 6/1998 | Lucas-Dean |
| 5,792,163 | A | 8/1998 | Hitzig |
| 5,792,169 | A | 8/1998 | Markman |
| 5,817,120 | A | 10/1998 | Rassman |
| 5,827,297 | A | 10/1998 | Boudjema |
| 5,895,403 | A | 4/1999 | Collinsworth |
| 5,922,000 | A | 7/1999 | Chodorow |
| 5,989,273 | A | 11/1999 | Arnold |
| 6,059,807 | A | 5/2000 | Boudjema |
| 6,120,521 | A | 9/2000 | Casparian |
| 6,258,111 | B1 * | 7/2001 | Ross et al. .................... 606/171 |
| 6,315,737 | B1 | 11/2001 | Skinner |
| 6,461,369 | B1 | 10/2002 | Kim |
| 6,482,178 | B1 | 11/2002 | Andrews et al. |
| 6,572,625 | B1 | 6/2003 | Rassman |
| 6,579,281 | B2 | 6/2003 | Palmer et al. |
| 6,601,748 | B1 | 8/2003 | Fung et al. |
| 6,641,564 | B1 | 11/2003 | Kraus |
| 6,669,685 | B1 | 12/2003 | Rizoiu et al. |
| 7,172,604 | B2 | 2/2007 | Cole |
| 7,261,721 | B2 | 8/2007 | Feller |
| 8,182,493 | B2 | 5/2012 | Cole |
| 8,202,279 | B2 | 6/2012 | Cole |
| 2002/0013572 | A1 | 1/2002 | Berlin |
| 2002/0099393 | A1 * | 7/2002 | Fleischman et al. ......... 606/153 |
| 2003/0040766 | A1 | 2/2003 | Werner |
| 2003/0097143 | A1 | 5/2003 | Mittelstaedt |
| 2003/0097144 | A1 | 5/2003 | Lee |
| 2003/0120297 | A1 | 6/2003 | Beyerlein |
| 2003/0233112 | A1 | 12/2003 | Alden et al. |
| 2003/0233114 | A1 * | 12/2003 | Merboth et al. .............. 606/185 |
| 2004/0193203 | A1 | 9/2004 | Pak et al. |
| 2004/0199195 | A1 | 10/2004 | Dumontelle |
| 2004/0260241 | A1 | 12/2004 | Yamamoto et al. |
| 2005/0075651 | A1 | 4/2005 | Ortiz |
| 2005/0187573 | A1 | 8/2005 | Rassman et al. |
| 2005/0267506 | A1 * | 12/2005 | Harris ........................... 606/187 |
| 2006/0072805 | A1 | 4/2006 | Tsipouras et al. |
| 2006/0273135 | A1 | 12/2006 | Beetel |
| 2007/0016100 | A1 * | 1/2007 | Miller ........................... 600/567 |

FOREIGN PATENT DOCUMENTS

| | | |
|---|---|---|
| WO | 0110307 | 2/2001 |
| WO | 03/096906 | 11/2003 |

OTHER PUBLICATIONS

Office action mailed Apr. 15, 2009 in co-pending U.S. Appl. No. 11/558,338, 13 pages.
Office action: Restriction Requirement mailed Apr. 1, 2009 in related matter U.S. Appl. No. 11/549,942, 8 pages.
Boudjema, "The FUExtractor® System: New Instrumentation to Improve Follicular Unit Extraction", Hair Transplantation Forum International, 1 page, Sep./Oct. 2006.
Unger et al., "Hair Transplantation", Fourth Edition, Revised and Expanded, pp. 353-354, Jan. 1, 2004.
Brandy, "New Instrumentation for Hair Transplantation Surgery", Dermatologic Surgery, Elsevier Science, New York, NY, vol. 24, No. 6, pp. 629-631, Jun. 1998.
Non-final Office action mailed Apr. 19, 2005 in related matter U.S. Appl. No. 10/795,835, 4 pages.
Amendment filed May 18, 2005 in related matter U.S. Appl. No. 10/795,835, 10 pages.
Non-final Office action mailed Jul. 12, 2005 in related matter U.S. Appl. No. 10/795,835, 9 pages.
Amendment filed Oct. 12, 2005 in related matter U.S. Appl. No. 10/795,835, 4 pages.
Non-final Office action mailed Jan. 4, 2006 in related matter U.S. Appl. No. 10/795,835, 7 pages.
Amendment filed May 2, 2006 in related matter U.S. Appl. No. 10/795,835, 11 pages.
Notice of Allowance mailed Aug. 1, 2006 in related matter U.S. Appl. No. 10/795,835, 6 pages.
Issue Fee and Formal Drawings filed Nov. 1, 2006 in related matter U.S. Appl. No. 10/795,835, 8 pages.
Issue Notification mailed Jan. 17, 2007 in related matter U.S. Appl. No. 10/795,835, 1 page.
Certificate of Correction filed Jun. 19, 2007 in related matter U.S. Appl. No. 10/795,835, 2 pages.
Certificate of Correction mailed Jul. 31, 2007 in related matter U.S. Appl. No. 10/795,835, 1 page.
European Search Report, in related matter PCT/US2004/023533, Dated Mar. 27, 2007, 81 pages.
Preliminary Amendment filed Aug. 17, 2006 in related matter U.S. Appl. No. 11/506,564, 7 pages.
Second Preliminary Amendment filed Nov. 9, 2006 in related matter U.S. Appl. No. 11/506,564, 13 pages.
Preliminary Amendment filed Nov. 30, 2006 in related matter U.S. Appl. No. 11/565,553, 18 pages.
Patent Application filed Jan. 3, 2006 in related matter U.S. Appl. No. 11/325,388, 46 pages.
Preliminary Amendment filed Nov. 9, 2006 in related matter U.S. Appl. No. 11/558,338, 18 pages.
Specification filed Mar. 9, 2007 in related matter U.S. Appl. No. 11/558,338, 51 pages.
Restriction Requirement mailed Dec. 10, 2008 in related matter U.S. Appl. No. 11/558,338, 7 pages.
Patent Application filed Oct. 16, 2006 in related matter U.S. Appl. No. 11/549,942, 29 pages.
International Search Report and Written Opinion mailed Jul. 24, 2008, in related matter No. PCT/US07/81519, 133 pages.
Response filed Jul. 14, 2009 in co-pending U.S. Appl. No. 11/558,338, 22 pages.
Office action: Restriction Requirement mailed Jun. 3, 2009 in related U.S. Appl. No. 11/549,942, 8 pages.
Response to Restriction Requirement filed Jul. 2, 2009 in related U.S. Appl. No. 11/549,942, 11 pages.
Office action: mailed Sep. 16, 2009 in U.S. Appl. No. 11/549,942, 19 pages.
Bernstein Medical Center for Hair Restoration, "Instrumentation for Three-Step FUE" 3 pages, www.bernsteinmedical.com/hair-transplant/follicular-extraction-Instrumentation.php, Jan. 2006.

(56) References Cited

OTHER PUBLICATIONS

Application as filed (U.S. Appl. No. 10/795,835, filed Mar. 9, 2004), 56 pages.
Notice to file missing parts mailed May 25, 2004 for U.S. Appl. No. 10/795,835, 2 pages.
Response to notice to file missing parts mailed Jun. 17, 2004 for U.S. Appl. No. 10/795,835, 2 pages.
Restriction Requirement mailed Apr. 19, 2005 for U.S. Appl. No. 10/795,835, 4 pages.
Response to Restriction Requirement mailed May 18, 2005 for U.S. Appl. No. 10/795,835, 11 pages.
Office Action mailed Jul. 12, 2005 for U.S. Appl. No. 10/795,835, 9 pages.
Office Action Response mailed Oct. 12, 2005 for U.S. Appl. No. 10/795,835, 5 pages.
Office Action mailed Jan. 4, 2006 for U.S. Appl. No. 10/795,835, 7 pages.
Office Action Response mailed May, 2, 2006 for U.S. Appl. No. 10/795,835, 12 pages.
Notice of Allowance mailed Aug. 1, 2006 for U.S. Appl. No. 10/795,835, 8 pages.
Issue Fee Payment, Corrected Drawings and Comments on Statement of Reasons for Allowance mailed Nov. 1, 2006 for U.S. Appl. No. 10/795,835, 9 pages.
Request for Certificate of Correction mailed Jun. 19, 2007 for U.S. Appl. No. 10/795,835, 5 pages.
Certificate of Correction mailed Jul. 31, 2007 for U.S. Appl. No. 10/795,835, 1 page.
Application as filed (U.S. Appl. No. 11/506,564, filed Aug. 17, 2006), 64 pages.
Notice to file missing parts mailed Sep. 5, 2006 for U.S. Appl. No. 11/506,564, 2 pages.
Response to notice to file missing parts mailed Nov. 1, 2006 for U.S. Appl. No. 11/506,564, 14 pages.
Second Preliminary Amendment mailed Nov. 9, 2006 for U.S. Appl. No. 11/506,564, 14 pages.
Filing Receipt mailed Nov. 9, 2006 for U.S. Appl. No. 11/506,564, 3 pages.
Rescission of Non-Publication Request mailed Aug. 27, 2008 for U.S. Appl. No. 11/506,564, 1 page.
Petition to Revive Application mailed Aug. 27, 2008 for U.S. Appl. No. 11/506,564, 8 pages.
Communication regarding Rescission of Non-Publication Request mailed Nov. 20, 2007 for U.S. Appl. No. 11/506,564, 4 pages.
Notice of Publication mailed Nov. 23, 2007 for U.S. Appl. No. 11/506,564, 2 pages.
Restriction Requirement mailed Dec. 8, 2009 for U.S. Appl. No. 11/506,564, 7 pages.
Response to Restriction Requirement mailed Feb. 8, 2010 for U.S. Appl. No. 11/506,564, 10 pages.
Office Action mailed Apr. 23, 2010 for U.S. Appl. No. 11/506,564, 12 pages.
Interview Summary mailed Aug. 4, 2010 for U.S. Appl. No. 11/506,564, 2 pages.
Office Action Response and Terminal Disclaimer mailed Aug. 23, 2010 for U.S. Appl. No. 11/506,564, 19 pages.
Decision on Terminal Disclaimer mailed Sep. 19, 2010 for for U.S. Appl. No. 11/506,564, 1 page.
Final Office Action mailed Nov. 29, 2010 for for U.S. Appl. No. 11/506,564, 15 pages.
Application as filed (U.S. Appl. No. 15/565,553, filed Nov. 30, 2006), 60 pages.
Notice to file missing parts mailed Sep. 5, 2006 for U.S. Appl. No. 11/565,553, 2 pages.
Filing Receipt mailed Jan. 16, 2007 for U.S. Appl. No. 11/565,553, 3 pages.
Response to notice to file missing parts mailed Jun. 1, 2007 for U.S. Appl. No. 11/565,553, 4 pages.
Updated Filing Receipt mailed Jun. 6, 2007 for U.S. Appl. No. 11/565,553, 3 pages.
Notice of Publication mailed Sep. 13, 2007 for U.S. Appl. No. 11/565,553, 1 page.
Restriction Requirement mailed Dec. 7, 2009 for U.S. Appl. No. 11/565,553, 7 pages.
Response to Restriction Requirement mailed Feb. 8, 2010 for U.S. Appl. No. 11/565,553, 18 pages.
Office Action mailed May 12, 2010 for U.S. Appl. No. 11/565,553, 18 pages.
Interview Summary mailed Aug. 4, 2010 for U.S. Appl. No. 11/565,553, 3 pages.
Office Action Response mailed Aug. 12, 2010 for U.S. Appl. No. 11/565,553, 27 pages.
Final Office Action mailed Nov. 5, 2010 for U.S. Appl. No. 11/565,553, 21 pages.
Interview Summary mailed Jan. 10, 2011 for U.S. Appl. No. 11/565,553, 1 page.
Application as filed (U.S. Appl. No. 11/325,388, filed Jan. 3, 2006), 66 pages.
Notice to file missing parts mailed Feb. 17, 2006 for U.S. Appl. No. 11/325,388, 2 pages.
References Response to notice to file missing parts mailed Feb. 17, 2006 for U.S. Appl. No. 11/325,388, 17 pages.
Restriction Requirement mailed Dec. 8, 2009 for U.S. Appl. No. 11/325,388, 7 pages.
Response to Restriction Requirement mailed Feb. 8, 2010 for U.S. Appl. No. 11/325,388 for U.S. Appl. No. 11/325,388, 13 pages.
Office Action mailed Apr. 27, 2010 for U.S. Appl. No. 11/325,388, 21 pages.
Office Action Response and Terminal Disclaimer mailed Jul. 27, 2010 for U.S. Appl. No. 11/325,388, 30 pages.
Notice of Non-Compliant Amendment mailed Aug. 3, 2010 for U.S. Appl. No. 11/325,388, 2 pages.
Interview Summary mailed Aug. 5, 2010 for U.S. Appl. No. 11/325,388, 3 pages.
Decision on Terminal Disclaimer mailed Aug. 27, 2010 for U.S. Appl. No. 11/325,388, 3 pages.
Office Action Response mailed Sep. 3, 2010 for U.S. Appl. No. 11/325,388, 27 pages.
Final Rejection mailed Nov. 24, 2010 for U.S. Appl. No. 11/325,388, 26 pages.
Application as filed (U.S. Appl. No. 11/508,669, filed Aug. 22, 2006), 108 pages.
Notice to file missing parts mailed Sep. 8, 2006 for U.S. Appl. No. 11/508,669, 2 pages.
Response to notice to file missing parts mailed Jan. 8, 2007 for U.S. Appl. No. 11/508,669, 7 pages.
Filing Receipt and Notice of Informal Application mailed Jan. 16, 2007 for U.S. Appl. No. 11/508,669, 4 pages.
Petition under 37 C.F.R. 1.78 and Preliminary Amendment mailed Jun. 4, 2007 for U.S. Appl. No. 11/508,669, 6 pages.
Notice of Publication mailed Jul. 5, 2007 for U.S. Appl. No. 11/508,669, 1 page.
Corrected Filing Receipt mailed Aug. 9, 2007 for U.S. Appl. No. 11/508,669, 3 pages.
Decision for Petition under 37 C.F.R. 1.78 and Corrected Filing Receipt mailed Aug. 13, 2007 for U.S. Appl. No. 11/508,669, 10 pages.
Notice of Publication mailed Dec. 20, 2007 for U.S. Appl. No. 11/508,669, 1 page.
Restriction Requirement mailed Dec. 8, 2009 for U.S. Appl. No. 11/508,669, 8 pages.
References Response to Restriction Requirement mailed Feb. 8, 2010 for U.S. Appl. No. 11/508,669, 20 pages.
Office Action mailed Apr. 28, 2010 for U.S. Appl. No. 11/508,669, 12 pages.
Office Action Response and Terminal Disclaimer mailed Jul. 28, 2010 for U.S. Appl. No. 11/508,669, 36 pages.
Interview Summary mailed Aug. 4, 2010 for U.S. Appl. No. 11/508,669, 4 pages.
Decision on Terminal Disclaimer mailed Sep. 1, 2010 for U.S. Appl. No. 11/508,669, 1 page.
Final Office Action mailed Oct. 26, 2010 for U.S. Appl. No. 11/508,669, 11 pages.

(56) References Cited

OTHER PUBLICATIONS

Application as filed (U.S. Appl. No. 11/558,338, filed Nov. 9, 2006), 55 pages.
Notice to file missing parts and filing recept mailed Jan. 12, 2007 for U.S. Appl. No. 11/558,338, 5 pages.
Response to notice to file missing parts mailed Mar. 9, 2007 for U.S. Appl. No. 11/558,338, 56 pages.
Updated Filing Receipt mailed Mar. 22, 2007 for U.S. Appl. No. 11/558,338, 3 pages.
Publication notice mailed Jun. 28, 2007 for U.S. Appl. No. 11/558,338, 1 page.
Restriction Requirement mailed Dec. 10, 2008 for U.S. Appl. No. 11/558,338, 7 pages.
Restriction Requirement Response mailed Feb. 2, 2009 for U.S. Appl. No. 11/558,338, 12 pages.
Office Action mailed Apr. 15, 2009 for U.S. Appl. No. 11/558,338, 7 pages.
Office Action Response mailed Jul. 14, 2009 for U.S. Appl. No. 11/558,338, 18 pages.
Office Action mailed Nov. 19, 2009 for U.S. Appl. No. 11/558,338, 9 pages.
Office Action Response mailed Feb. 18, 2010 for U.S. Appl. No. 11/558,338, 25 pages.
Final Office Action mailed Aug. 3, 2010 for U.S. Appl. No. 11/558,338, 19 pages.
Final Office Action Response mailed Oct. 4, 2010 for U.S. Appl. No. 11/558,338, 21 pages.
Advisory Action mailed Oct. 28, 2010 for U.S. Appl. No. 11/558,338, 2 pages.
Request for Continued Examination mailed Nov. 3, 2010 for U.S. Appl. No. 11/558,338, 21 pages.
Written Opinion mailed Sep. 13, 2005 for PCT/US04/0423533, 3 pages.
Publication of Application mailed Oct. 13, 2005 for PCT/US04/023533, 49 pages.
Article 19 Publication mailed Dec. 29, 2005 for PCT/US04/023533, 6 pages.
Preliminary Report on Patentability for PCT/US04/023533, 4 pages.
EP Filing Documents for EP National stage mailed Oct. 9, 2006 for EP04778857.5, 7 pages.
Publication Notice mailed Nov. 15, 2006 for EP04778857.5, 1 page.
European Search Report mailed Mar. 27, 2007 for EP04778857.5, 5 pages.
Official Letter from EPO mailed Jul. 27, 2007 for EP04778857.5, 1 page.
Article 94(3) communication mailed Feb. 20, 2008 for EP04778857.5, 8 pages.
Application as field, mailed Jan. 3, 2007 for PCT/US07/060056, 68 pages.
Notification concerning Submission or Transmittal of Priority Document mailed Jan. 14, 2007 for PCT/US07/060056, 1 page.
Publication of ISR mailed Aug. 2, 2007 for PCT/US07/060056, 2 pages.
Entry into EP phase mailed Jun. 6, 2008 for PCT/US07/060056, 3 pages.
Written Opinion mailed Jul. 16, 2008 for PCT/US07/060056, 9 pages.
Notification Concerning Transmittal of International Preliminary Report of Patentability for PCT/US07/060056, 2 pages.
Non-Final Office Action response, mailed Aug. 23, 2011 for U.S. Appl. No. 11/506,564, 27 pages.
Non-Final Office Action response, mailed Sep. 9, 2011 for U.S. Appl. No. 11/325,388, 43 pages.
Non-Final Office Action, mailed Jun. 24, 2011 for U.S. Appl. No. 11/558,338, 19 pages.
Notice of Allowance and issue fee dues, mailed Jan. 20, 2012, for U.S. Appl. No. 11/506,564, 15 pages.
Issue fee payment, mailed Apr. 20, 2012, for U.S. Appl. No. 11/506,564, 8 pages.
Issue notification, mailed May 2, 2012, for U.S. Appl. No. 11/506,564, 1 page.
Application as filed on May 14, 2012, for U.S. Appl. No. 13/471,307, 66 pages.
Filing receipt and notice to file missing parts, mailed May 25, 2012, for U.S. Appl. No. 13/471,307, 6 pages.
Applicant response to notice to file missing parts, mailed Jul. 25, 2012 for U.S. Appl. No. 13/471,307, 71 pages.
Updated filing receipt, mailed Aug. 10, 2012, for U.S. Appl. No. 13/471,307, 4 pages.
Final Office Action, mailed Feb. 29, 2012 for U.S. Appl. No. 11/325,388, 27 pages.
Request for continued examination, mailed Jul. 30, 2012, for U.S. Appl. No. 11/325,388, 52 pages.
Notice of Allowance mailed Dec. 23, 2011 for U.S. Appl. No. 11/558,338, 8 pages.
Issue Fee payment, mailed Mar. 23, 2012, for U.S. Appl. No. 11/558,338, 13 pages.
Issue Notification, mailed May 30, 2012, for U.S. Appl. No. 11/558,338, 1 page.
Application as filed on Apr. 16, 2012, for U.S. Appl. No. 13/448,232, 65 pages.
Filing receipt and notice to file missing parts, mailed May 2, 2012, for U.S. Appl. No. 13/448,232, 6 pages.
Applicant response to notice to file missing parts, mailed Jul. 2, 2012 for U.S. Appl. No. 13/448,232, 68 pages.
Updated filing receipt, mailed Jul. 12, 2012, for U.S. Appl. No. 13/448,232, 5 pages.
U.S. Appl. No. 13/471,307 / Notice of Publication Mailed Nov. 23, 2012, 1 Page.
U.S. Appl. No. 13/471,307 / Non-Final Office Action, Mailed Jun. 11, 2013, 12 pages.
U.S. Appl. No. 13/471,307 / Response after Non-Final Office Action, Mailed Sep. 11, 2013, 1 Page.
U.S. Appl. No. 13/471,307 / Final Rejection, Mailed Dec. 31, 2013, 13 Pages.
U.S. Appl. No. 13/471,307 / Request for Continued Examination (RCE), Mailed Mar. 31, 2013, 3 Pages.
U.S. Appl. No. 11/565,553 / Non-Final Rejection, Mailed Mar. 21, 2013, 28 Pages.
U.S. Appl. No. 11/565,553 / Response after Non-Final Office Action, Mailed Jun. 21, 2013, 1 Page.
U.S. Appl. No. 11/565,553 / Final Rejection, Mailed Jan. 7, 2014, 33 Pages.
U.S. Appl. No. 11/565,553 / Request for Continued Examination (RCE), Mailed Apr. 7, 2014, 3 Pages.
U.S. Appl. No. 11/325,388 / Non-Final Office Action, Mailed Oct. 25, 2012, 26 Pages.
U.S. Appl. No. 11/325,388 / Response to Non-Final Office Action, Mailed Jan. 25, 2013, 1 Page.
U.S. Appl. No. 11/325,388 / Final Rejection, Mailed Oct. 9, 2013, 26 Pages.
U.S. Appl. No. 11/325,388 / Response After Final Action, Mailed Jan. 9, 2014, 1 Page.
U.S. Appl. No. 11/325,388 / Terminal Disclaimer review decision, Mailed Jan. 15, 2014, 1 Page.
U.S. Appl. No. 11/325,388 / Notice of Allowance and Fees Due (PTOL-85), Mailed Jan. 30, 2014, 9 Pages.
U.S. Appl. No. 13/448,232 / Notice of Publication, Mailed Oct. 18, 2012, 1 Page.
U.S. Appl. No. 13/448,232 / Non-Final Office Action, Mailed Jan. 29, 2013, 16 Pages.
U.S. Appl. No. 13/448,232 / Terminal Disclaimer as Filed on Apr. 29, 2013, 1 Page.
U.S. Appl. No. 13/448,232 / Response to Non-Final Office Action, Mailed Apr. 29, 2013, 1 Page.
U.S. Appl. No. 13/448,232 / Terminal Disclaimer Review Decision, Mailed May 1, 2-13, 1 Page.

* cited by examiner

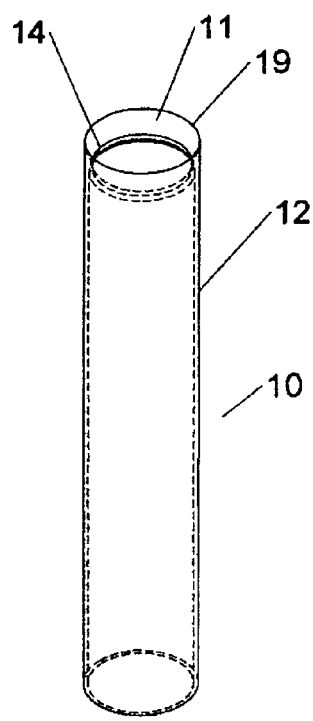
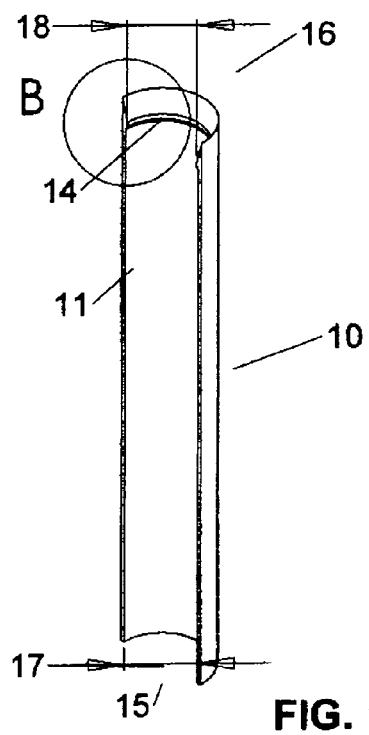
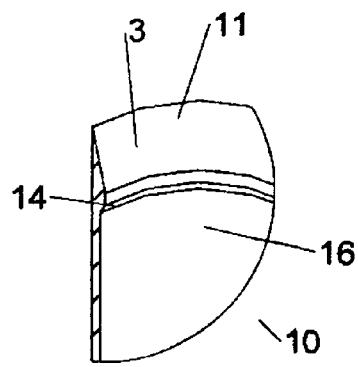
DETAIL B
FIG. 1a  FIG. 1b  FIG. 1c
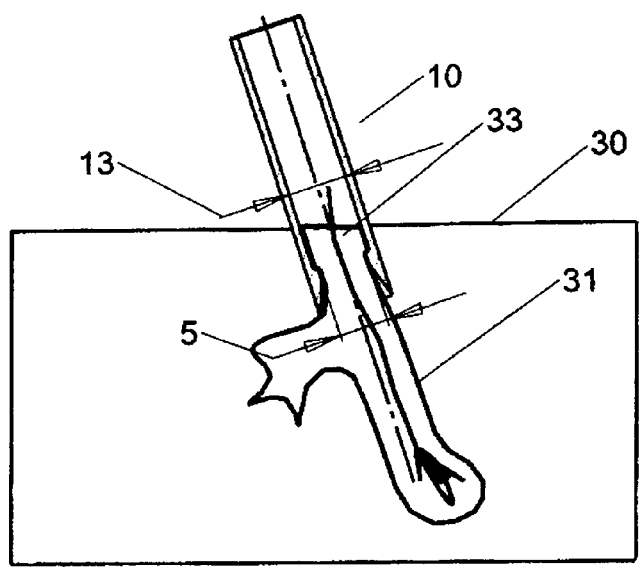
FIG. 1d

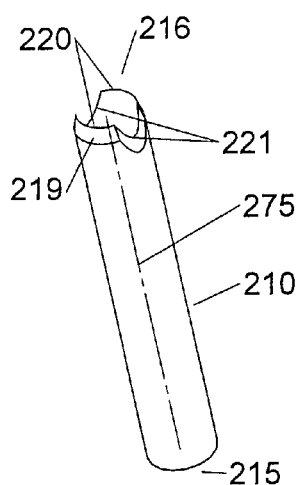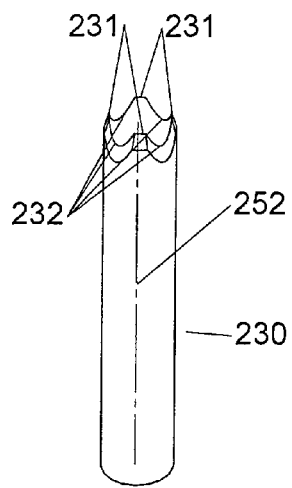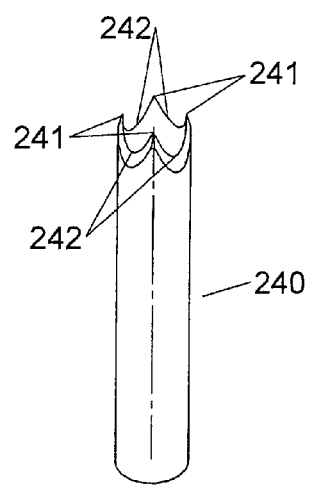
FIG. 2a  FIG. 2b  FIG. 2c
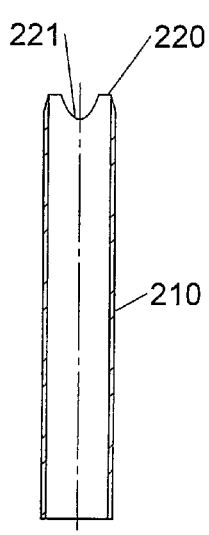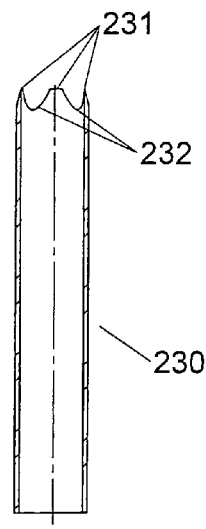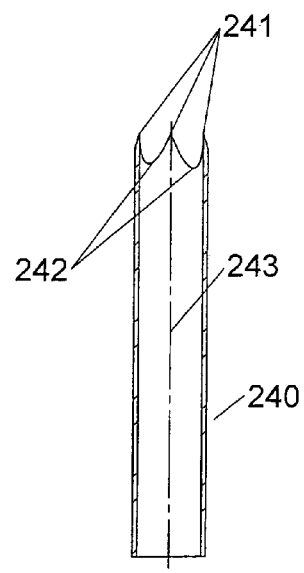
FIG. 2d  FIG. 2e  FIG. 2f

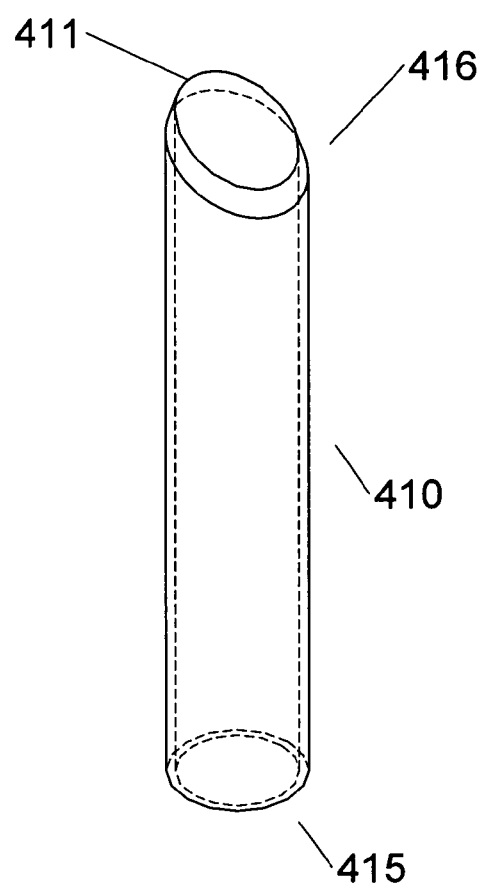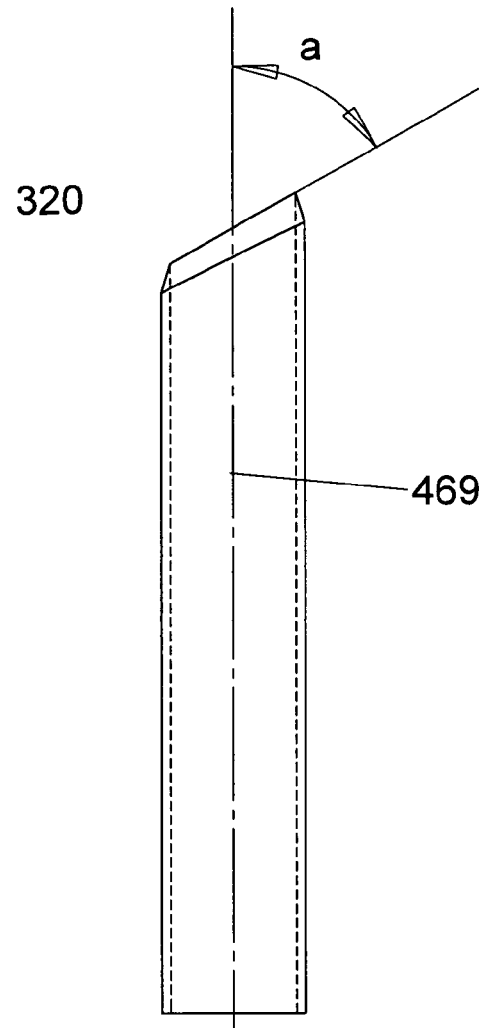
FIG. 4a
FIG. 4b

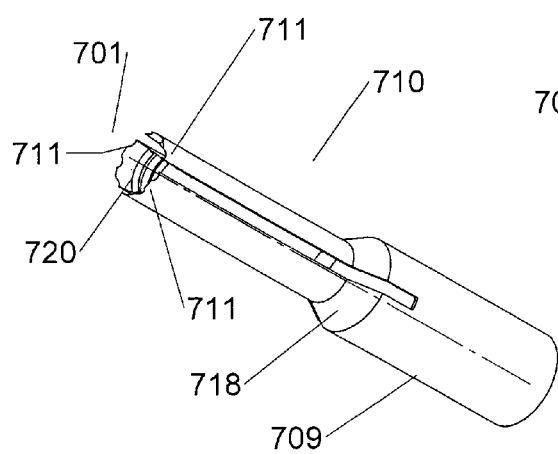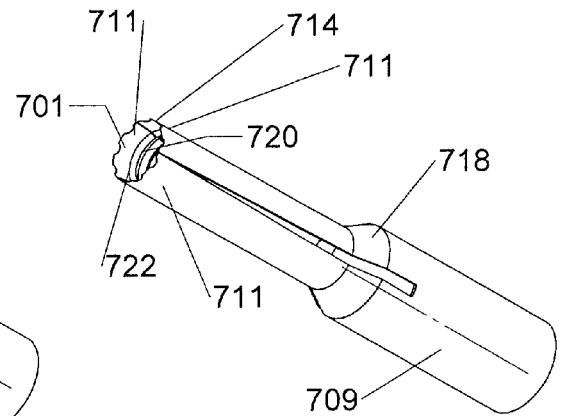
FIG. 7a  FIG. 7b
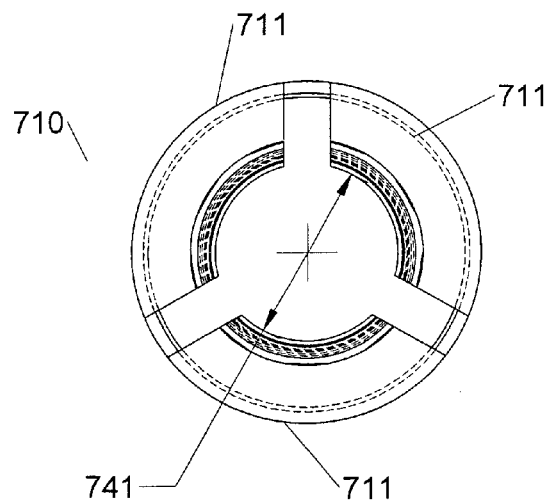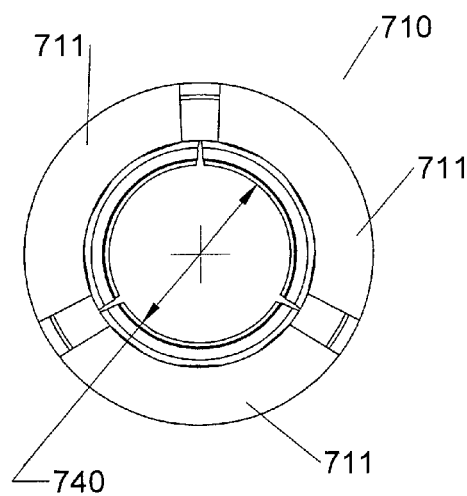
FIG. 7c  FIG. 7d

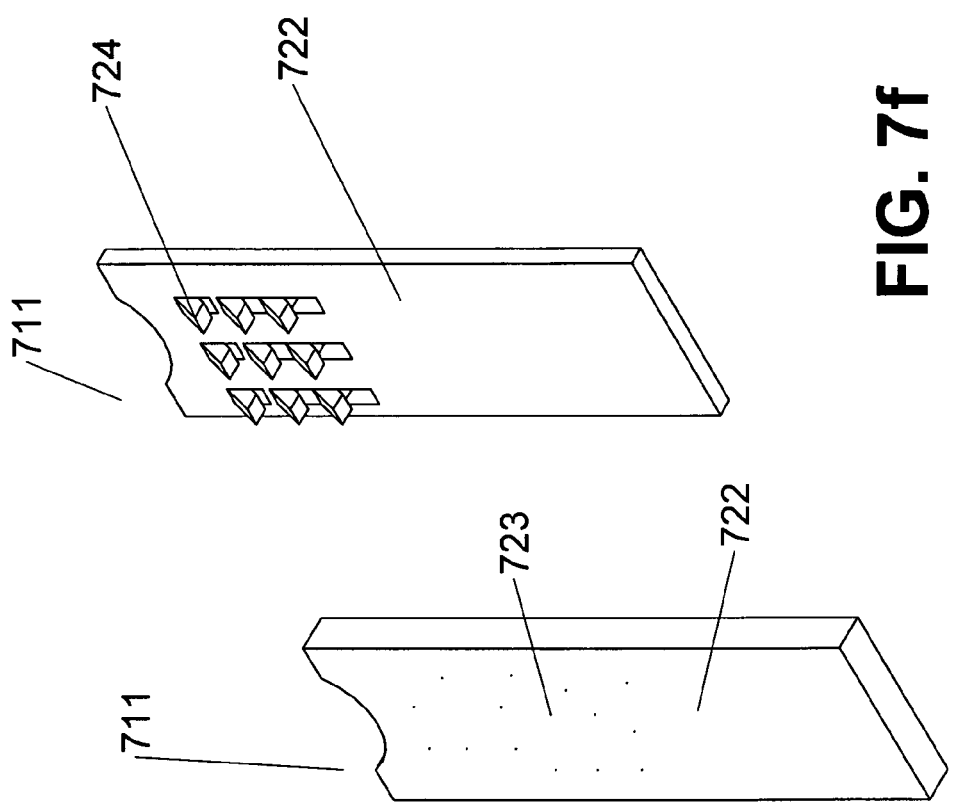

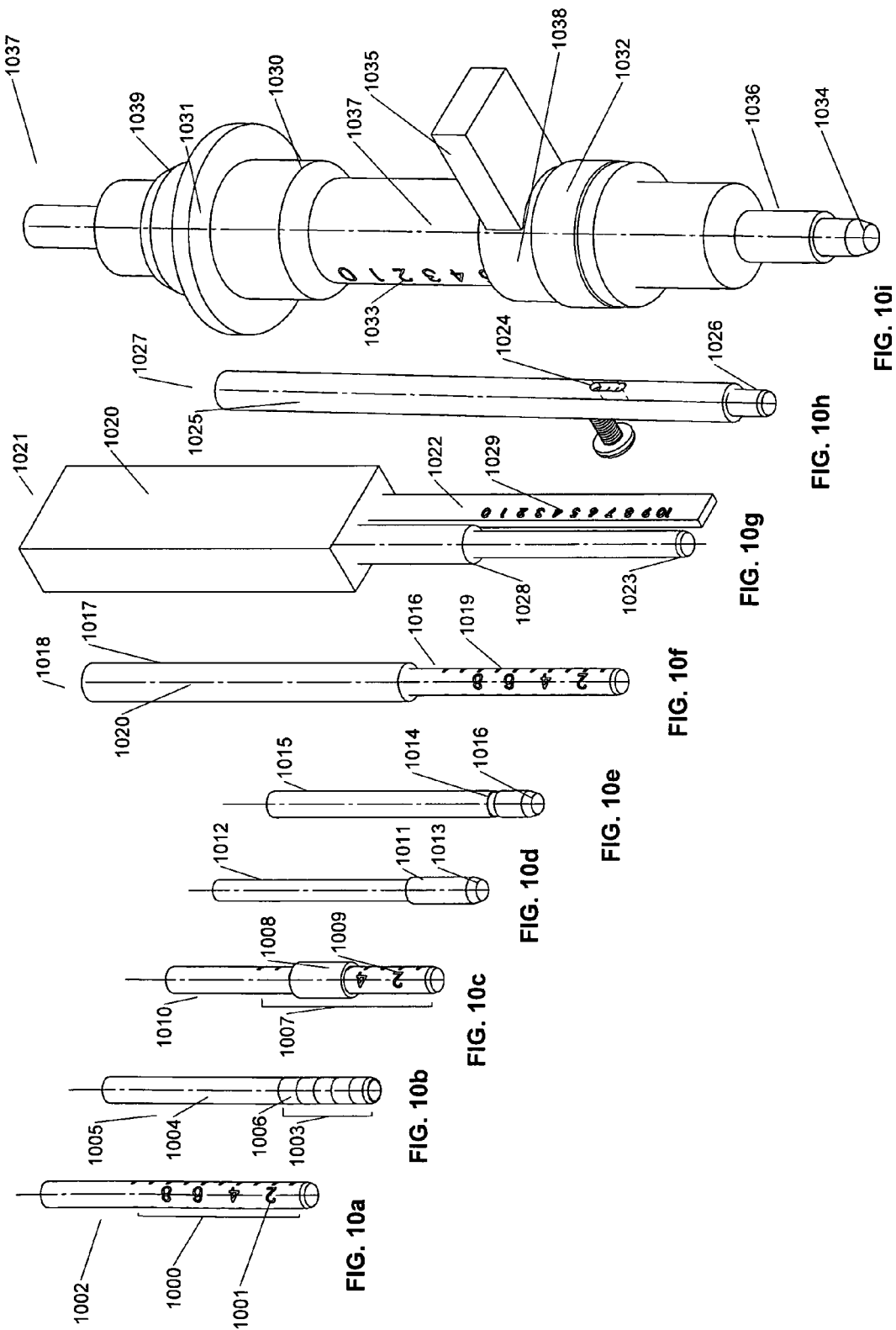

FOLLICULAR DISSECTION DEVICE AND METHOD

RELATED APPLICATION

This is a continuation-in-part of U.S. patent application Ser. No. 11/325,388, entitled "Enhanced Follicular Dissection Punch and Method, which was filed on Jan. 3, 2006, now U.S. Pat. No. 8,753,354 which in turn is a continuation-in-part of U.S. patent application Ser. No. 10/795,835, filed Mar. 9, 2004, entitled Follicular Extraction Punch And Method, now issued as U.S. Pat. No. 7,172,604.

BACKGROUND

1. Field

This disclosure relates to surgical instruments and methods for extracting hair follicles.

2. Background Information

Devices may be used in hair transplantation or other procedures involving dissection of mammalian tissue.

BRIEF DESCRIPTION OF THE DRAWINGS

FIG. 1a is a diagram of a punch according to an embodiment.

FIG. 1b is a diagram of a punch according to an embodiment.

FIG. 1c is a partial cross-section view of a punch according to an embodiment.

FIG. 1d is a cross-section of a punch during a follicular dissection procedure according to an embodiment.

FIG. 2a is a diagram of a punch according to an embodiment.

FIG. 2b is a diagram of a punch according to an embodiment.

FIG. 2c is a diagram of a punch according to an embodiment.

FIG. 2d is a cross-section of a punch according to an embodiment.

FIG. 2e is a cross-section of a punch according to an embodiment.

FIG. 2f is a cross-section of a punch according to an embodiment.

FIG. 4a is a diagram of a punch according to an embodiment.

FIG. 4b is a side view of a punch according to an embodiment.

FIG. 7a is a diagram of a punch according to an embodiment.

FIG. 7b is a diagram of a punch in FIG. 7a in a closed position according to an embodiment.

FIG. 7c is an end view of a punch according to an embodiment.

FIG. 7d is an end view of a punch according to an embodiment.

FIG. 7e is a diagram showing a partial view of a member according to an embodiment.

FIG. 7f is a diagram showing a partial view of a member according to an embodiment.

FIG. 10a is a diagram of a depth marker scale applied to the cylindrical body of a punch.

FIG. 10b is a diagram of a color depth marker applied to a punch.

FIG. 10c is a diagram of a depth marker sliding ring applied to a punch.

FIG. 10d is a diagram of a depth marker step or shoulder applied to a punch.

FIG. 10e is a diagram of a depth marker groove applied to a punch.

FIG. 10f is a diagram of depth marker with sliding handle applied to a punch.

FIG. 10g is a diagram of a depth marker with sliding scale applied to a punch.

FIG. 10h is a diagram of a depth marker on a punch with a viewing window.

FIG. 10i is a diagram of a depth stop with a sliding collar and handle on a graduated barrel.

DETAILED DESCRIPTION

Figure 3:
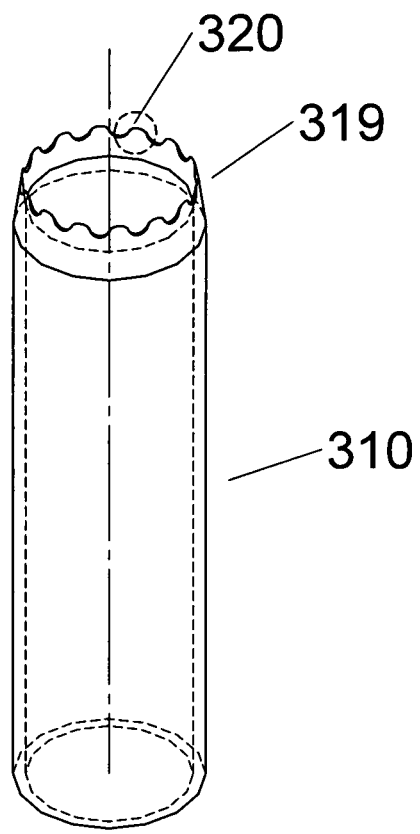
FIG. 3 is a diagram of a punch according to an embodiment.

In the following detailed description, numerous specific details are set forth in order to provide a thorough understanding of claimed subject matter. However, it will be understood by those skilled in the art that claimed subject matter may be practiced without these specific details. In other instances, well-known methods, procedures, and components have not been described in detail so as not to obscure claimed subject matter.

In a follicular dissection procedure a follicular dissection instrument having a punch may be used. In a particular embodiment, a punch may have a substantially cylindrical shape with an outside diameter, an inside diameter and a longitudinal length. A punch may have a uniform or varying diameter. A punch may have one or more edges. In a particular embodiment, one or more edges may be used for dissecting tissue and referred to as a cutting edge and/or cutting edges. A cutting edge may be located on an outside diameter, an inside diameter or in between outer and inner diameters. A cutting edge and/or edges may have a variety of configurations, such as, for instance, being serrated, sharp or dull. Additionally, multiple cutting edges may be located on the cylindrical surface at some angle to the axis. However, these are merely examples of configurations which may characterize a cutting edge and claimed subject matter is not limited is this respect. A cutting edge may be configured by a variety of methods such as for instance machining and/or electrochemical etching or electrochemical polishing. Additionally, punches may be made of a variety of materials such as for example stainless steel, titanium, or other metal alloy and the area around the cutting edge may be surface coated with hard thin films like TiN. However, these are merely examples of punches, materials and methods of configuring a cutting edge and claimed subject matter is not so limited.

In various embodiments, at least one punch may be coupled to a Powered Follicular Isolation Device (PFID). In a particular embodiment, a PFID may comprise any one of a variety of mechanized graft dissection devices capable of causing rotating, reciprocating, vibrating, translating and/or oscillating motion of a punch. A PFID may be further capable of extending and retracting a punch along a longitudinal axis.

FIGS. 1a-1d illustrate various perspective views of a particular embodiment of a punch. Referring to FIG. 1a, in a particular embodiment, a punch 10 may have a cutting edge 19, an inner surface 11 and an outer surface 12. Inner surface 11 may have a shelf 14.

FIG. 1c, illustrates a partial cross-section of punch 10 showing shelf 14 between a first inner surface 11 and a second inner surface 16. As can be seen in FIG. 1c, an outcrop, such as, shelf 14 occurs where inner diameter (not shown) of punch 10 changes.

FIG. 1b illustrates a cutaway view of a particular embodiment of punch 10. In a particular embodiment, punch 10 may have a first end 15 and a second end 16. Punch 10 may also have a first inner diameter 17 nearer first end 15 and a second inner diameter 18 nearer shelf 14 at second end 16. First inner diameter 17 may be greater than second inner diameter 18. First inner diameter 17 and second inner diameter 18 may be separated by shelf 14 on inner surface 11 of punch 10.

Referring again to FIG. 1c, a main bevel edge 3 is located on inner surface 11. During a dissection procedure, a compressive force (not shown) may be substantially imparted to a graft thus pushing the graft towards the center away from the cutting edge. This may result in a partially dissected graft remaining within a punch 10. An outer surface 12 may also have a beveled edge (not shown) in addition to the inner bevel on surface 11, enabling some of the compressive force (not shown) to be applied to the area surrounding a graft. There may be beveling on outer surface 12. However, this is merely an example of a configuration of beveled edges on a punch and claimed subject matter is not limited in this respect.

Referring again to FIG. 1a, during a dissection procedure, a tissue graft (not shown) may be held within punch 10, due to a gradual increase in diameter of inner surface 11. In a particular embodiment, as a diameter of inner surface 11 increases beyond shelf 14, a tissue graft (not shown) may relax or expand to fill the additional space within first inner diameter 17 and thereby secure itself within punch 10. Additionally, in a particular embodiment, due to the increasing diameter of inner surface 11, friction force to extract a tissue graft may be reduced thus enabling a decreased cutting force during a dissection procedure. It should be understood, however, a punch may have more than one outcrop or shelf on an inner surface and may have more than two inner diameters and claimed subject matter is not limited in this respect.

FIG. 1d, illustrates a cutaway view of a particular embodiment of punch 10 (shown in FIG. 1a) in use during a follicular dissection procedure. In a particular embodiment, punch 10 may be inserted into skin 30 around a hair follicle 31. According to a particular embodiment, inner diameter 13 may be greater than inner diameter 5. Tissue 33 may expand to fill punch 10 at inner diameter 13 as punch 10 is inserted into skin 30.

FIGS. 1a-1d illustrate various perspective views of a particular embodiment of a punch 10. In a particular embodiment, punch 10 may, additionally, be coupled to a PFID (not shown). As pointed out above, a PFID may enable rotating, reciprocating, vibrating, translating and/or oscillating motion of a punch 10, and may be further capable of extending and retracting a punch 10 along a longitudinal axis.

FIGS. 2a-2c illustrate various embodiments of a punch having multiple cutting edges. FIGS. 2d-2f show cross-sections of punches shown in FIGS. 2a-2c. It is to be understood that the following is a description of examples of particular embodiments of punches that may be used in follicular dissection procedures. The description of the following particular embodiments is meant to be illustrative and claimed subject matter is not limited in this regard. In a particular embodiment, punches illustrated in FIGS. 2a-2f may additionally, be coupled to a PFID (not shown). However, this is merely an example of a way to utilize punches illustrated in FIGS. 2a-2f and claimed subject matter is not limited in this regard.

Referring to FIG. 2a, depicting a particular embodiment of a punch 210. In a particular embodiment, punch 210 may have a first end 215 and a second end 216. Second end 216 may comprise a first relief face 219. There may be relief face under edge 220 and/or 221. First relief face 219 may be formed by beveling second end 216 of punch 210 creating multiple and/or varied cutting edges. Punch 210 may have at least one primary cutting edge 220 and at least one secondary cutting edge 221. FIG. 2a illustrates a punch 210 having two primary cutting edges 220 and two secondary cutting edges 221. In a particular embodiment, primary cutting edges 220 may be separated from each other by secondary cutting edges 221. Secondary cutting edges 221 may be recessed with respect to primary cutting edges 220. According to a particular embodiment, secondary cutting edges 221 may be beveled cutting edges on planes inclined or angled with respect to longitudinal axis 275. Beveling of cutting edges 221 may be at an angle between the plane containing the cutting edge and the longitudinal axis. Such an angle may be between 5° to 60°. Primary cutting edges 220 as well as secondary cutting edges 221 may take on a variety of configurations. For instance, primary cutting edge 220 may comprise a top edge having a substantially flat planar shape in a plane substantially normal to longitudinal axis 275 of punch 210. Secondary cutting edge 221 may comprise a substantially a variety of shapes such as, for instance, straight and/or arced shape. Such secondary cutting edge may reside in a plane substantially oblique to longitudinal axis 275.

Punch 210 may be coupled to a PFID (not shown) during a follicular dissection procedure. Using a punch 210 during a follicular dissection procedure, as described, may result in a reduction in the cutting force required during the dissection process and may reduce twisting of the tissue during dissection. During a dissection procedure, twisting of the skin may result from tangential forces at the cutting edges. Twisting of the skin may be reduced where secondary cutting edges 221 of punch 210 cut the skin rather than twist the skin in the direction of rotation of punch 210. In addition, the contact area between punch 210 and the skin may be reduced because portions of second end 216 may be recessed. Here, a cutting force and twisting moments may be reduced because the amount of required cutting force and twisting moments is proportional to the contact area.

Referring now to FIG. 2*d*, punch 210 is shown in cross-section. Primary cutting edge 220 and secondary cutting edge 221 are shown adjacent one another. The substantially arced shape of secondary cutting edge 221 can be seen in a particular embodiment.

Referring to FIG. 2*b*, in a particular embodiment, punch 230 may have four primary cutting edges 231 and four secondary cutting edges 232. Additionally, depending on the application or type of follicular dissection being used a primary cutting edge 231 may have a variety of tips such as, for instance, a substantially sharp or dull tip. Secondary cutting edges 232 may have a substantially arced shape and may lie in a plane substantially oblique to longitudinal axis 252.

FIG. 2*e* illustrates punch 230 in cross-section. In a particular embodiment, primary cutting edge 231 and secondary cutting edge 232 are shown adjacent one another. Depending on the application or type of follicular dissection technique being used a secondary cutting edge 232 may be sharp or dull and may be arced or may have a variety of shapes. Primary cutting edge 231 may be sharp or dull and may have a variety of shapes such as rounded or polygonal.

Referring to FIG. 2*c*, in a particular embodiment, a punch 240 may have four primary cutting edges 241 and four secondary cutting edges 242. According to a particular embodiment, primary cutting edges 241 may form substantially sharp points. Secondary cutting edges 242 may have substantially arced shapes. During dissection, primary cutting edges 241 may pierce the skin with minimum force. This may reduce deformation of the skin such as occurs using conventional methods of follicular dissection. When punch 240 is rotated, vibrated, translated or oscillated, secondary cutting edges 242 may cut the skin in the direction of rotation which may additionally reduce a twisting or torsional moment of skin during a follicular dissection procedure.

Referring now to FIG. 2*f*, punch 240 is shown in cross-section. In a particular embodiment, primary cutting edge 241 and secondary cutting edge 242 may be adjacent to one another. Secondary cutting edge 242 may have a substantially arced shape. FIGS. 2*a*-2*f* depict examples of shapes, angles and numbers of primary and secondary cutting edges of a punch and claimed subject matter is not limited in this regard.

FIG. 3, in a particular embodiment, a punch 310 may have a denticulated edge 319 which may have a variety of tips such as, for instance, a substantially sharp or dull tip. Denticulations 320 of the denticulated edge 319 may be a variety shapes such as deep or shallow scallops, round, square, pointed or jagged and may be uniform or may comprise a number of shapes. However, these are merely examples of how denticulations may be shaped according to a particular embodiment and claimed subject matter is not so limited. Additionally, denticulations 320 may have various dimensions and claimed subject matter is not limited to any specific dimensions. Denticulation 320 my have a sharp edge on the front end or on one side or on both sides of the arc. Use of punch 310 may help prevent transection of a hair follicle (not shown) during a follicular dissection procedure. According to a particular embodiment, movement in various directions may facilitate dissection by punch 310. For instance, linear axial, rotating, vibrating, oscillating and/or reciprocating motions may enable dissection with punch 310. The dissection process may be performed partially by a combination of circumferential and axial motions and/or performed partially by only axial motion and/or circumferential motions. In a particular embodiment, punch 310 may be coupled to a PFID (not shown) during a follicular dissection procedure. However, this is merely an example of a way to use a punch during a follicular dissection procedure and claimed subject matter is not limited in this regard.

Figure 4C:
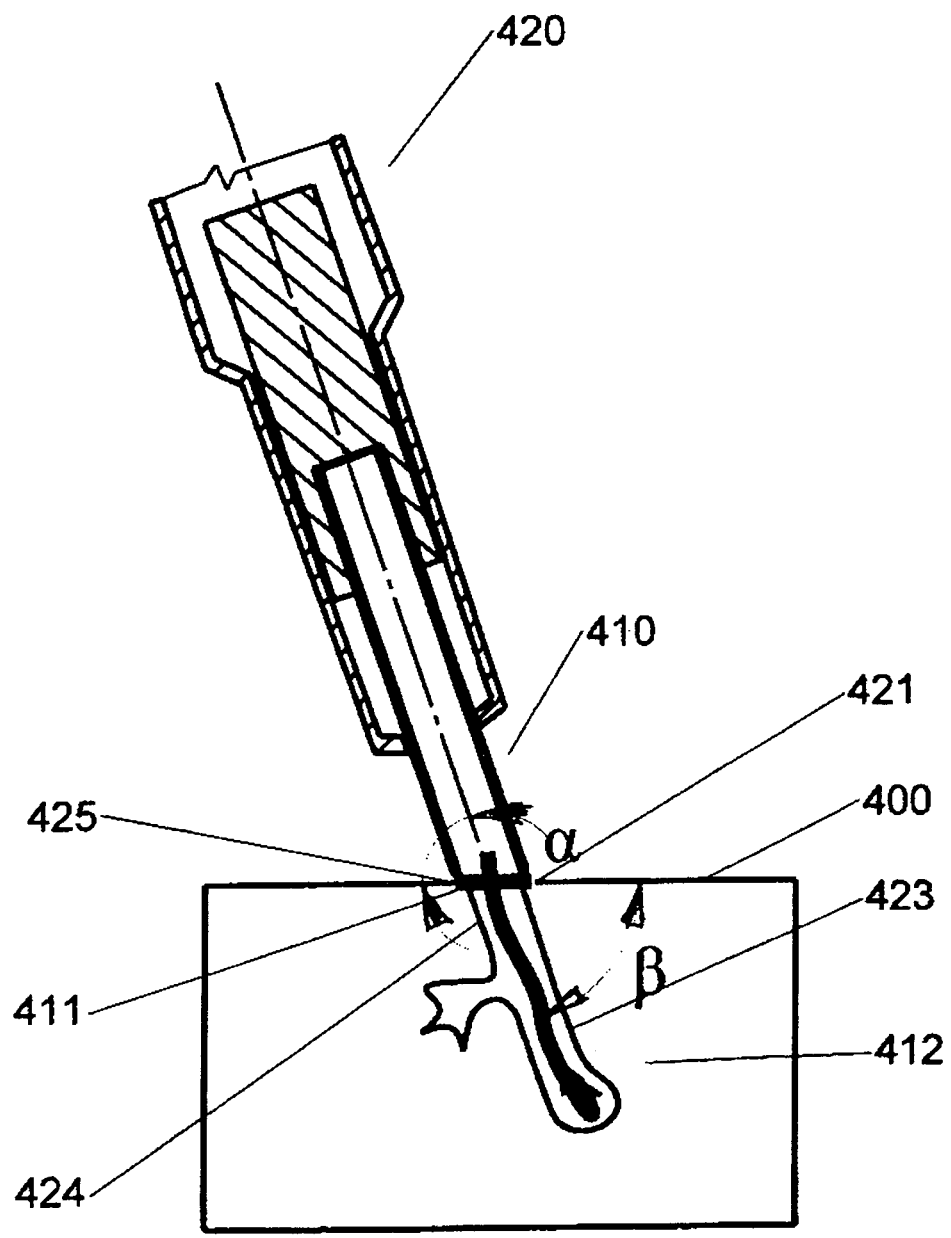
FIG. 4c is a cross-sectional view of a punch during a follicular dissection procedure according to an embodiment.

FIGS. 4*a*-4*c* depict a punch 410. FIG. 4*a*, illustrates a particular embodiment of punch 410. According to a particular embodiment, punch 410, may have a first end 415, a second end 416, and a longitudinal axis 409 (as shown in FIG. 4*b*) extending from first end 415 to second end 416. Second end 416 may have a cutting edge 411. As illustrated in FIG. 4*b*, cutting edge 411 may be set at an angle α with respect to longitudinal axis 409.

Referring to FIG. 4*c*, in a particular embodiment, a punch 410 may be assembled to a follicular dissection device 420 (partial assembly), such as, for instance a PFID. According to a particular embodiment, a punch 410 may be used in a follicular dissection procedure. A hair follicle 412 may have an angle of follicular growth β. β may be taken with respect to a surface of skin 400 of a patient. Angle α may be substantially equivalent to an angle of follicular growth β. Punch 410 having an angled cutting edge 411 may enable a user to extract hair follicle 412 at its angle of growth β, thus reducing a risk of transecting hair follicle 412 during the follicular dissection procedure. The transection risk may be reduced further by aligning cutting edge 411 flat to skin 400 while the punch axis is aligned to the hair follicle axis and prior to dissecting a follicular graft. Such alignment may substantially eliminate deformation of skin 400. Such deformation of skin 400 may cause hair follicle 412 to bend and expose hair follicle 412 to cutting edge 411, thus increasing the risk of transection. Uniform contact between a punch 410 and skin 400 may result in application of a uniform force (not shown) around cutting edge 411. Such uniform application of force may eliminate a bending moment and thus bending of the skin 400 resulting in reduction in transection of a follicular graft. Additionally, a profile of punch 410 may be oriented such that the longer side 421 of punch 410 may be aligned with respect to side 423 of follicle 412. Shorter side 425 of punch 410 thus may not go far enough into follicle 412 to transect side 424 of follicle 412. Additionally, use of punch 410 may enable a reduction in a dissection diameter (not shown) during a follicular dissection procedure. A smaller dissection diameter may result in a smaller scar size left after a follicular dissection. In a particular embodiment, a 1 mm punch may leave a scar size reduced by about 15% compared to conventional methods of follicular dissection. However, FIGS. 4a-4c merely illustrate and example of a punch having an angle and claimed subject matter is not limited in this regard.

Figure 5:
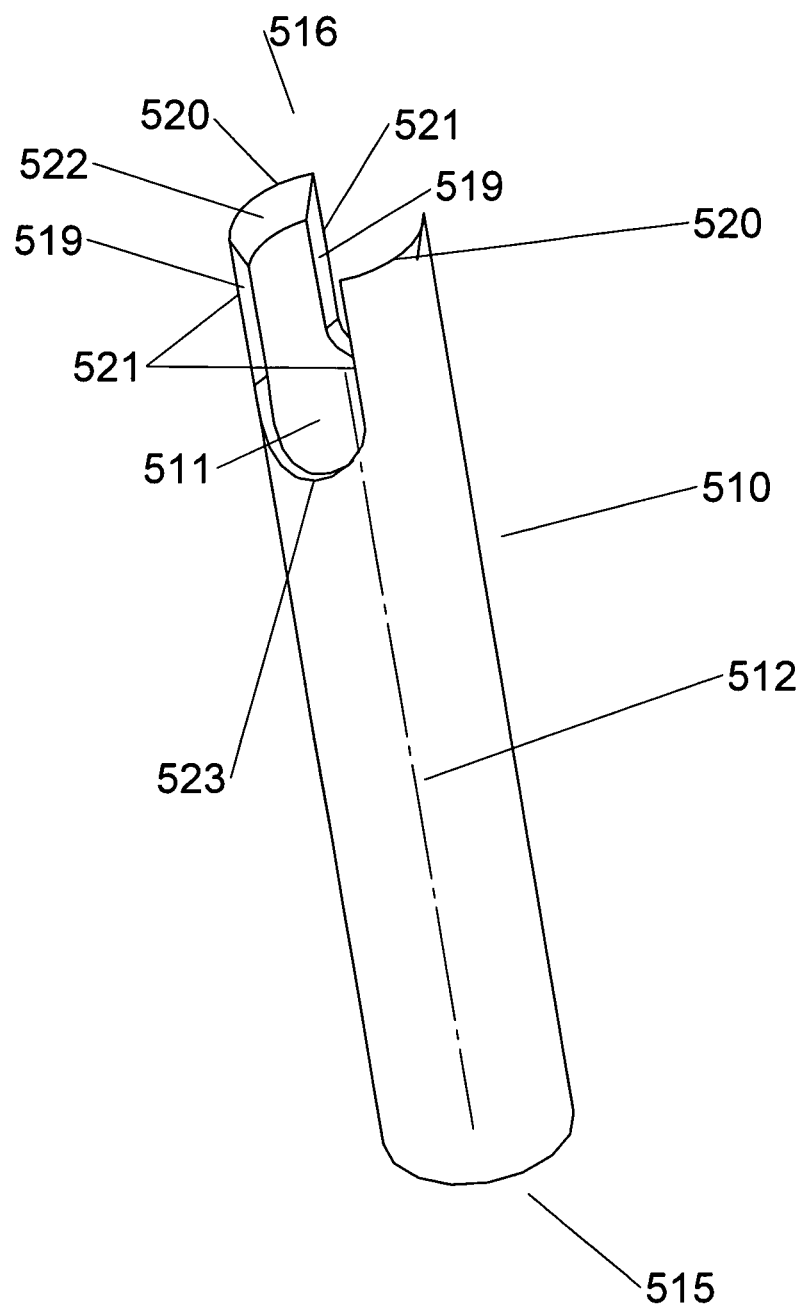
FIG. 5 is a diagram of a punch according to an embodiment.

Referring to FIG. 5, according to a particular embodiment, a punch 510 may have a first end 515 and a second end 516, and extend along a longitudinal axis 512 from first end 515 to second end 516. Located at second end 516 may be at least one primary cutting edge 520 and at least one secondary cutting edge 521. The primary cutting edge 520 may be formed, for instance, by machining and/or etching a bevel 522 at an angle with respect to the longitudinal axis 512. Secondary cutting edge 521 may be formed, for instance, by machining and/or etching out at least one slot 511 of a particular depth in the direction of longitudinal axis 512 and forming bevel 519 in a direction perpendicular to longitudinal axis 512. FIG. 5 depicts punch 510 having two primary cutting edges 520 and two secondary cutting edges 521. According to a particular embodiment, primary cutting edges 520 may be separated from each other by secondary cutting edges 521. Primary cutting edges 520 may be elevated with respect to secondary cutting edges 521 therefore secondary cutting edges 521 may be recessed. Primary cutting edges 520, as well as secondary cutting edges 521 may take on a variety of configurations. In a particular embodiment, for instance, primary cutting edge 520 may comprise a top edge having a substantially flat planar shape in a plane substantially normal to longitudinal axis 512. Secondary cutting edge 521 may comprise a lower edge 523 having a substantially arced shape and lie in a plane substantially parallel to longitudinal axis 512.

Continuing with FIG. 5, a user may perform a follicular dissection using punch 510 by pushing punch 510 into skin (not shown) along longitudinal axis 512, to enable primary cutting edges 520 to perform a cutting action. When punch 510 is rotated, vibrated, translated or oscillated, the main cutting action may be performed by secondary cutting edges 521. In a particular embodiment, a dissection procedure may be performed in part by a combination of circumferential and axial motions and/or by a circumferential motion up to a certain depth and then only axial motion. Using a punch 510, as described during a follicular dissection procedure, may enable a reduction in the cutting force applied during the dissection process and may reduce twisting of the tissue during dissection due to the cutting action of the secondary cutting edges in the circumferential direction. In a particular embodiment, slots 511 may also enable visualization of the graft being dissected. Punch 510 may be coupled to a PFID (not shown) allowing linear axial movement and/or a rotating, vibrating, oscillating and/or a reciprocating motion or a combination of these motions. Such motion may facilitate dissection using punch 510. However, this is merely an example of particular configurations of a punch having primary and secondary cutting edges and slots and claimed subject matter is not limited in this respect.

FIGS. 6a-6e illustrate a punch 610 having collapsible and expandable members according to a particular embodiment. Punch 610 may be coupled to a PFID which may enable movement of a punch 610. Follicular dissection may be facilitated using punch 610 with a linear axial movement and/or a rotating motion, an oscillating motion and/or a reciprocating motion or any combination of these motions. However, these are merely examples of devices and motions that may facilitate follicular dissection using a punch and claimed subject matter is not limited in this regard.

Figure 6A:
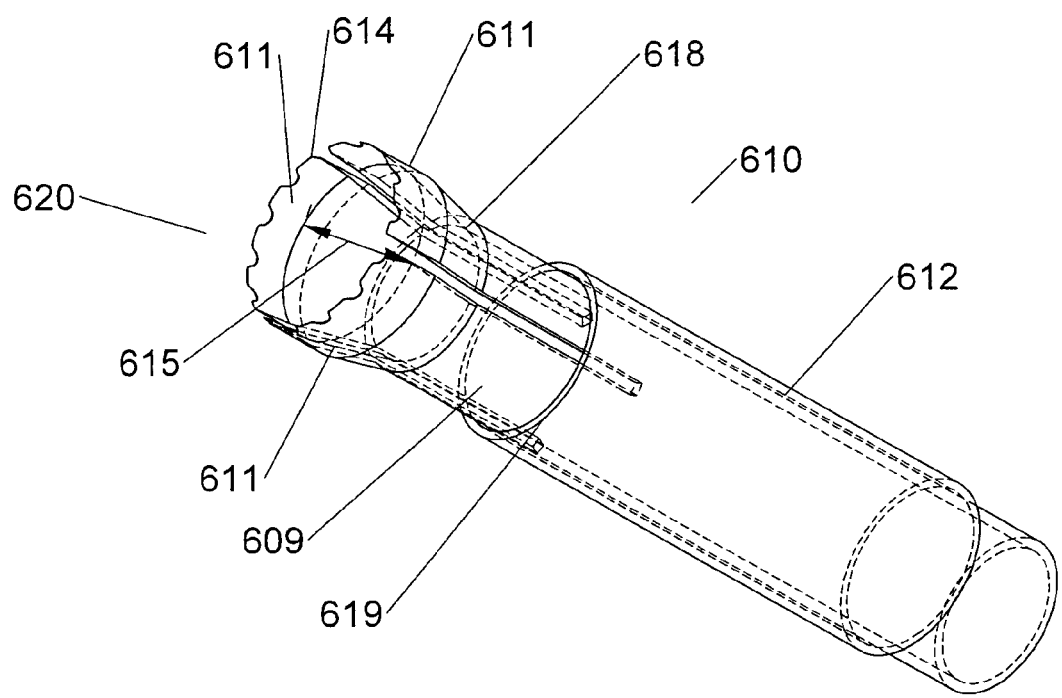
FIG. 6a is a diagram of a punch according to an embodiment.

FIG. 6a depicts a particular embodiment of a punch 610 having at least two members 611 coupled at a base portion 609. In the particular embodiment depicted in FIG. 6a, punch 610 comprises three members 611. A housing 612 may partially enclose at least a base portion 609, of members 611. A mechanism coupling members 611 may allow members 611 to be collapsed and expanded by application of force against housing 612. Such force may be transmitted to members 611 through a base portion by a variety of methods, such as, for instance, an actuator (not shown) may be coupled to members 611 and may impart a force via manual adjustment or automated adjustment. FIG. 6a depicts members 611 in an expanded configuration. Collapsing and expanding members 611 may change the inside diameter 615 of punch 610 in response to mechanical or electromechanical means, for example. However, these are merely examples of ways in which members 611 may be collapsed or expanded, and claimed subject matter is not limited in this respect.

In a particular embodiment, axial motion between punch 610 and housing 612 may result when a force is applied to housing 612. A force applied to housing 612 may move members 611 in a radial direction which in turn may change the diameter of punch 610 at tip 620. Inclined surface 618 may be coupled to housing 612 such that members 611 may be pressed together or relaxed a certain amount depending on the position of edge 619 of housing 612 on inclined surface 618. However, this is merely an example of a method of moving members 611 and claimed subject matter is not limited in this respect.

In a particular embodiment, members 611 may have a cutting edge 614. Such a cutting edge 614 may be serrated or may have a variety of configurations. For instance, cutting edge 614 may be sharp, dull, straight, arced or denticulated without departing from the scope of claimed subject matter.

Figure 6B:
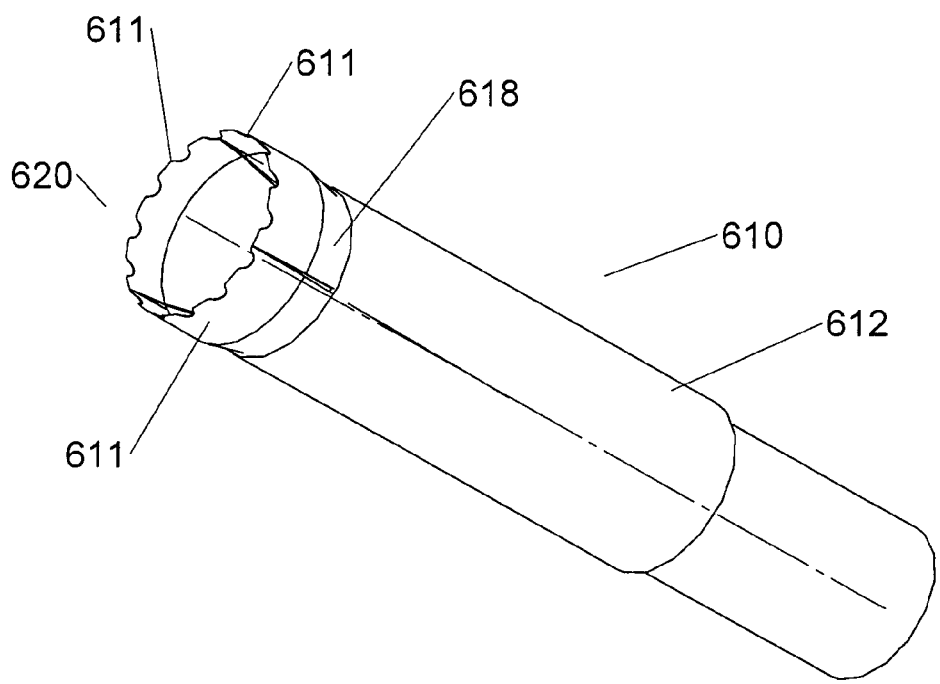
FIG. 6b is a diagram of a punch according to an embodiment.

FIG. 6b illustrates a particular embodiment of a punch 610. In a particular embodiment, members 611 of punch 610 may be collapsed. Members 611 may be configured to collapse at tip 620 as punch housing 612 moves into a position adjacent inclined surface 618. Additionally, members 611 may also be fully or partially closed or opened by positioning the housing at a particular position on inclined surface 618. According to a particular embodiment, members 611 may also be collapsed by keeping the housing 612 stationary and pulling punch 610 into housing 612. However, these are merely examples of ways in which members may be opened or collapsed and claimed subject matter is not limited in this regard.

Figure 6C:
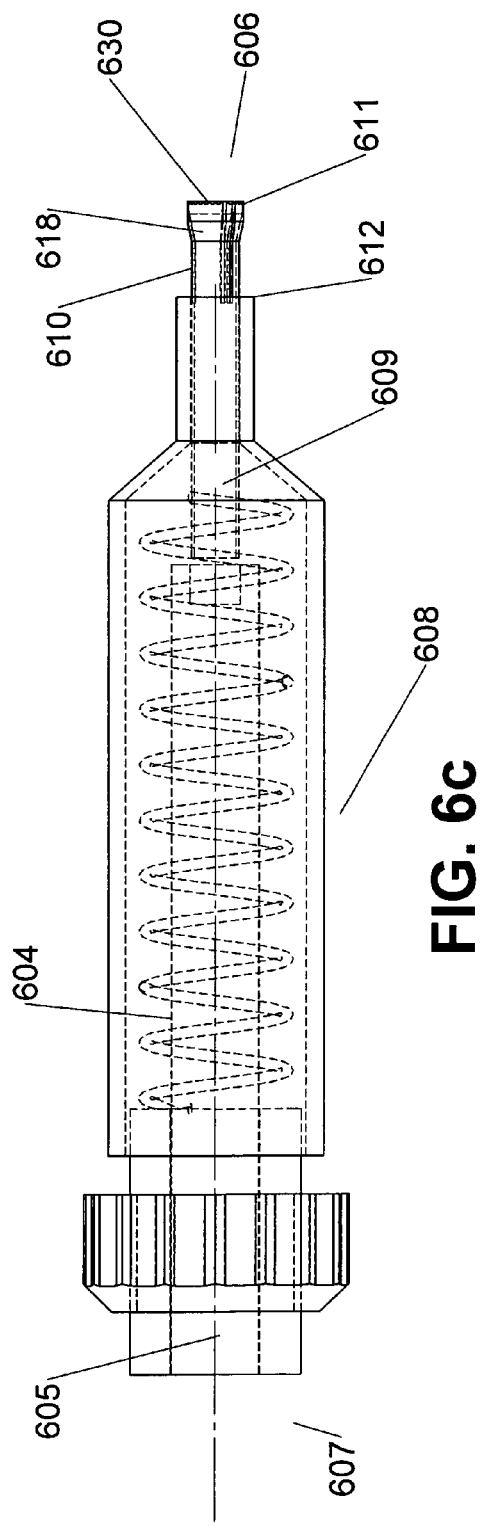
FIG. 6c is a diagram showing a detail view of a punch as depicted in FIG. 6a according to an embodiment.
Figure 6D:
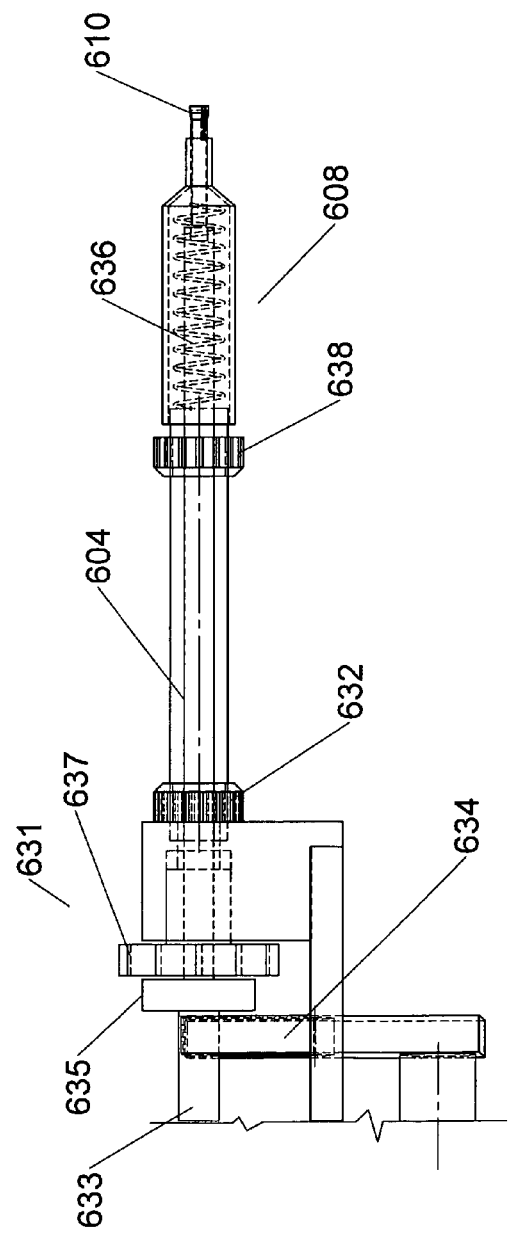
FIG. 6d is a diagram of a punch as depicted in FIG. 6a assembled to a follicular dissection instrument (partial view) according to an embodiment.

FIG. 6c is a detailed view of the partial assembly of the follicular dissection device illustrated in FIG. 6d. Punch 610 is shown assembled in a follicular dissection device 608. In a particular embodiment, follicular dissection device 608 may have a first end 607 and a second end 606, and extend along a longitudinal axis 605 between first end 607 and second end 606. According to a particular embodiment, members 611 may maintain a substantially constant diameter when inclined surface 618 is not in contact with housing 612 or when the housing is kept at one position on inclined surface 618. A mechanical member 604 may be capable of axial translation, vibration, oscillation and/or rotation about longitudinal axis 605. According to a particular embodiment, mechanical member 604 may be coupled to base 609 of members 611 such that motion of mechanical member 604 may cause members 611 to move. Such movement may, for instance, collapse or expand members 611 in response to axial translation of mechanical member 604 with respect to punch 610 in housing 612. Additionally, members 611 may be collapsed at tip 630 as mechanical member 604 moves into a particular position at base 609. Alternatively, members 611 may collapse to a specific position and be kept constant for a certain procedure. However, this is merely an example of a particular embodiment of a punch having a particular configuration with respect to a housing and follicular dissection device and claimed subject matter is not limited in this respect.

FIG. 6d illustrates punch 610 and dissection device 608 coupled to a powered follicular isolation device (PFID) 631 (shown partially). In a particular embodiment, end 607 may be fixed to PFID 631 by a counter nut 638. However, this is merely an example of a method of attaching a PFID to a punch 610 in a particular embodiment. In other embodiments, a PFID may be attached for instance, by using a mechanical means and/or adhesives and claimed subject matter is not limited in this respect.

In a particular embodiment, PFID 631 may enable motion of mechanical member 604. For instance, such motion may be provided in response to rotation of an electric motor of PFID 631 and which may be converted to a rotating or oscillating motion by PFID 631. According to a particular embodiment, output of PFID 631 may be transferred to mechanical member 604. Mechanical member 604 may be connected to an output shaft 633 fixedly coupled to a collar 635 and actuated by fork 634 driven by a solenoid or manually (not shown). Fork 634 may move collar 635, coupled to output shaft 633 forward from a first position against a spring 636 until stopped by the depth stop 637 at a second position.

A spring 636 may return mechanical member 604 to a first position such that the process may repeat when motion is being transferred by means of PFID 631. However, this is merely an example of a way to enable movement of a punch and claimed subject matter is not limited in this regard.

Figure 6F:
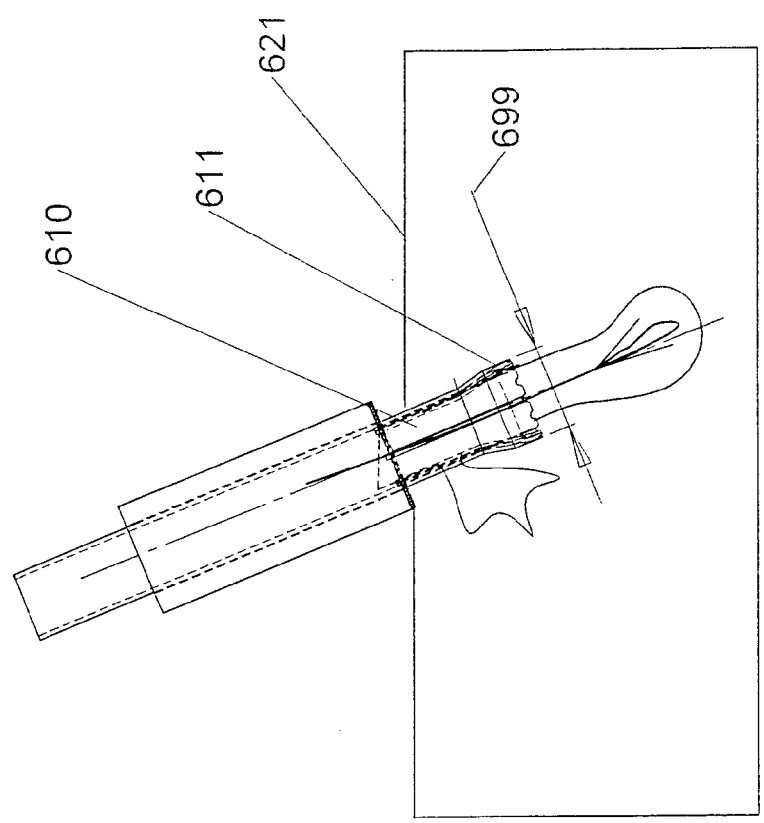
FIG. 6f is a diagram of a punch during a second phase of a follicular dissection procedure according to an embodiment.
Figure 6E:
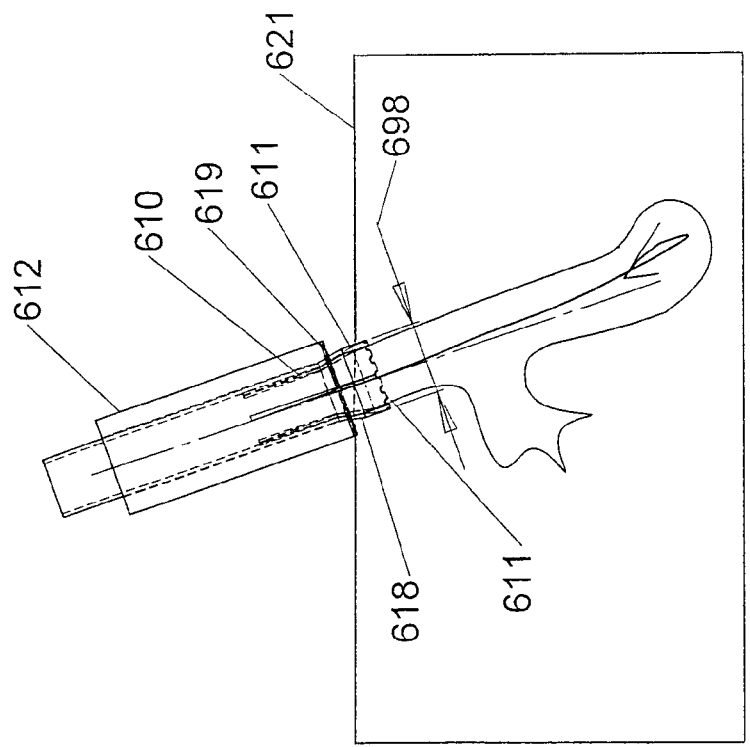
FIG. 6e is a diagram of a punch during a first phase of a follicular dissection procedure according to an embodiment.

Referring now to FIG. 6e, in a particular embodiment, members 611 may be set to expand to a first diameter 698 during a first phase of a follicular dissection procedure where tissue 621 may be initially scored. A specific first diameter 698 of members 611 may be set by positioning an outside inclined surface 618 of punch 610 to a specific position with respect to edge 619 of punch housing 612. However, this is merely an example of a method of setting members to a first diameter in a particular embodiment and claimed subject matter is not limited in this respect.

FIG. 6f illustrates a particular embodiment of a punch 610 with members 611 set to a second diameter 699 during a second phase of the follicular dissection procedure after punch 610 has been inserted into tissue 621. Such setting of members 611 to a second diameter 699 may be convenient for a user who may score tissue 621 during a first phase of a follicular dissection procedure to a first diameter 698 (as shown in FIG. 6e) and then may wish to expand the punch diameter upon deeper incision into tissue 621 to a second punch diameter 699 during a second phase of a follicular dissection procedure. Such ability to set variable dissection diameters may enable a reduction of the risk of transecting the grafts. However, this is merely an example of a method of setting members to various diameters and claimed subject matter is not limited in this respect.

Figure 7G:
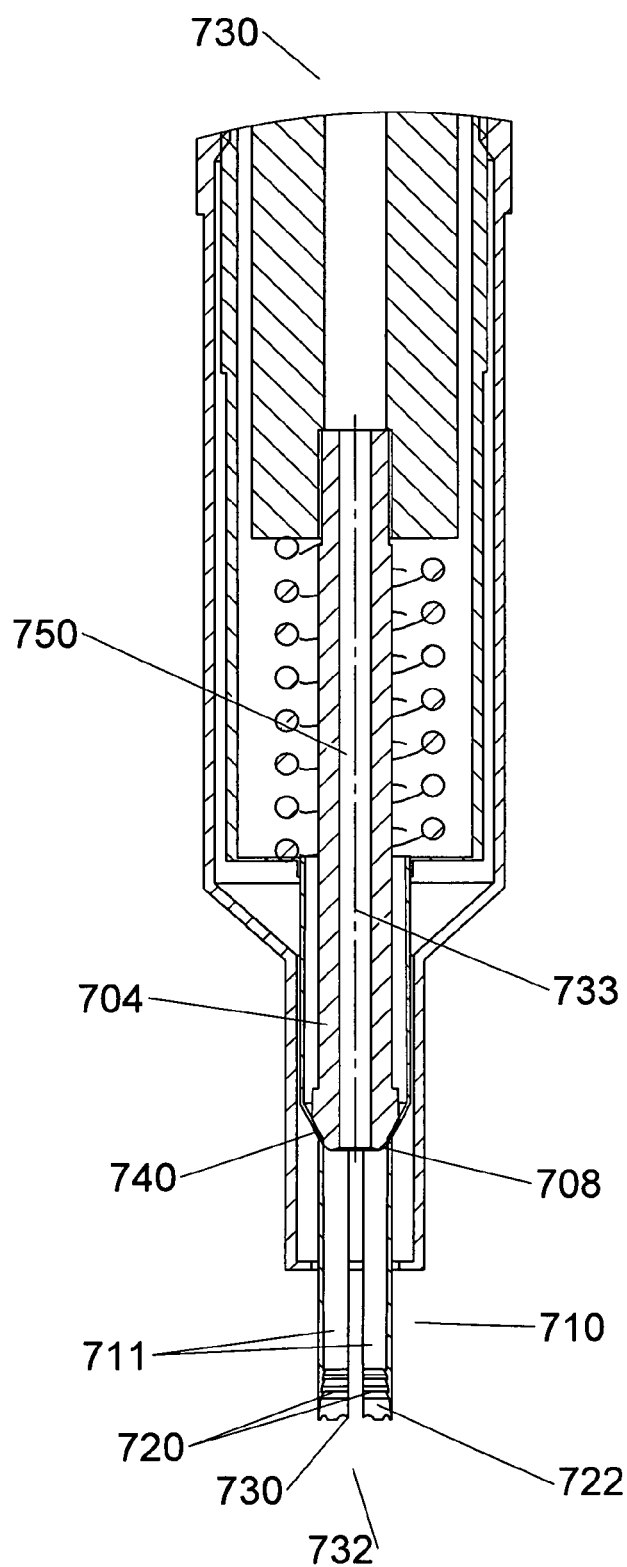
FIG. 7g is a diagram showing a partial assembly view of a punch in the open position according to an embodiment.

FIGS. 7a-7h depict a punch having collapsible and expandable members with graft extracting features according to a particular embodiment. In FIG. 7a, punch 710 may have at least two members 711 coupled to a base 709 and comprise three members 711. Here, coupling of base 709 of members 711 may allow members 711 to be collapsed and expanded by application of a force (not shown). Such force may be transferred to members 711 by a variety of devices, such as, for instance, via a mechanical member, as discussed above in FIG. 6a or via an actuator such as a housing, also discussed with reference to FIG. 6a. Such a mechanical member or actuator may impart a force on the inclined surface 718 of the base 709 by manual adjustment or automated adjustment. However, this is merely an example of a variety of devices capable of imparting a force on members and claimed subject matter is not limited in this respect. Returning to FIG. 7a, collapsing and expanding members 711 may change an inside diameter (as depicted in FIGS. 7c-7d) of punch 710. However these are merely examples of ways in which to transfer force to and move members of a punch and claimed subject matter is not limited in this respect.

FIG. 7b, depicts a particular embodiment of members 711 designed with follicular extracting features, such as barbs 720, to facilitate removal of a follicular graft. During a follicular dissection procedure, as punch 710 is being removed from the skin of a patient, members 711 may collapse. In a particular embodiment, barbs 720 may be positioned on inner surface 722 of members 711 and may point away from end 701. According to a particular embodiment, barbs 720 may penetrate a follicular tissue graft being extracted and secure it as punch 710 is being withdrawn from the skin of the patient. However this is merely an example of a follicular extracting feature and claimed subject matter is not limited in this regard.

FIGS. 7e-7f illustrate various inside surfaces 722 of members 711. FIG. 7e illustrates a particular embodiment of a follicular extracting feature to facilitate removal of a follicular tissue graft as illustrated above. Such follicular extracting features may comprise, for example, a textured inner surface 723 of members 711 and may enable substantially secure removal of a follicular tissue graft by gripping the tissue as it is pulled. Referring to FIG. 7f, any of a variety of protrusions 724 extending outward from inner surface 722 of members 711 may also enable substantially secure removal of a follicular tissue graft. However, these are merely examples of follicular extraction features and claimed subject matter is not limited in this regard.

Referring again to FIG. 7b, punch 710 with members 711 are depicted in a collapsed position at end 701. In a particular embodiment, punch 710 may have a cutting edge 714. Cutting edge 714 may be serrated. However, in another embodiment, cutting edge 714 may have a variety of configurations; for example, cutting edge 714 may be sharp or dull and straight or angled without departing from of claimed subject matter. However, these are merely examples of cutting edges of a punch and claimed subject matter in not limited in this regard.

FIGS. 7c-7d, depict various inside diameters of punch 710. Members 711 are shown in a collapsed or expanded position at end 701 of punch 710. FIG. 7d, depicts members 711 adjusted to a collapsed position. Punch 710 may have a first inside diameter 740. In FIG. 7c members 711 are adjusted to an expanded position and punch 710 may have a second inside diameter 741. Inside diameter 741 may be greater than inside diameter 740 from FIG. 7d. As described in reference to FIGS. 6d-6e, members 711 may be set to expand to a first inside diameter 740 during a first phase of a follicular dissection procedure where tissue may be initially scored. Then members 711 may be set to a second inside diameter 741 during a second phase of the follicular dissection procedure after punch 710 has been inserted into tissue. This ability may enable a user who may score tissue during a first phase of a follicular dissection procedure at a first punch diameter and wish to expand the punch diameter upon deeper incision into tissue to a second punch diameter during a second phase of a follicular dissection procedure. However, this is merely an example of using variable diameter features of a punch and claimed subject matter in not limited in this regard.

Referring to FIG. 7g, depicting a partial assembly of a follicular dissecting device, in a particular embodiment, a punch 710 may have a first end 731 and a second end 732, and extend along a longitudinal axis 733 between first end 731 and second end 732. According to a particular embodiment, a mechanical member 704 such as, for instance, a mandrel may be capable of translation along longitudinal axis 733 and may act on inside inclined surface 740 of members 711 such that translation of mechanical member 704 may cause members 711 to collapse or expand in response to translation of mechanical member 704.

According to a particular embodiment, members 711 may collapse at tip 730 as mechanical member 704 is retracted moving toward first end 731 to a particular position adjacent inside inclined surface 740. Members 711 may expand at tip 730 as mechanical member 704 is extended moving toward second end 732 to a particular position adjacent inside inclined surface 740. However, this is merely an example of ways in which members may be set and claimed subject matter is not limited in this regard.

In a particular embodiment, a member 711 may be designed with follicular extracting features such as barbs 720. Barbs 720 may be positioned on inner surface 722 of members 711 and may point away from end 732. During a follicular dissection procedure, as punch 710 is being removed from the skin of a patient, members 711 may collapse and barbs 720 may penetrate the follicular tissue being extracted. Barbs 720 may secure tissue as punch 710 is being withdrawn from the skin of the patient. Also, a suction force may be applied via portal 750 in mechanical member 704 to aid in the secure dissection of tissue grafts during a follicular dissection procedure. However, this is merely an example of ways to secure tissue grafts when using a punch during a follicular dissection procedure and claimed subject matter is not limited in this respect.

Figure 7H:
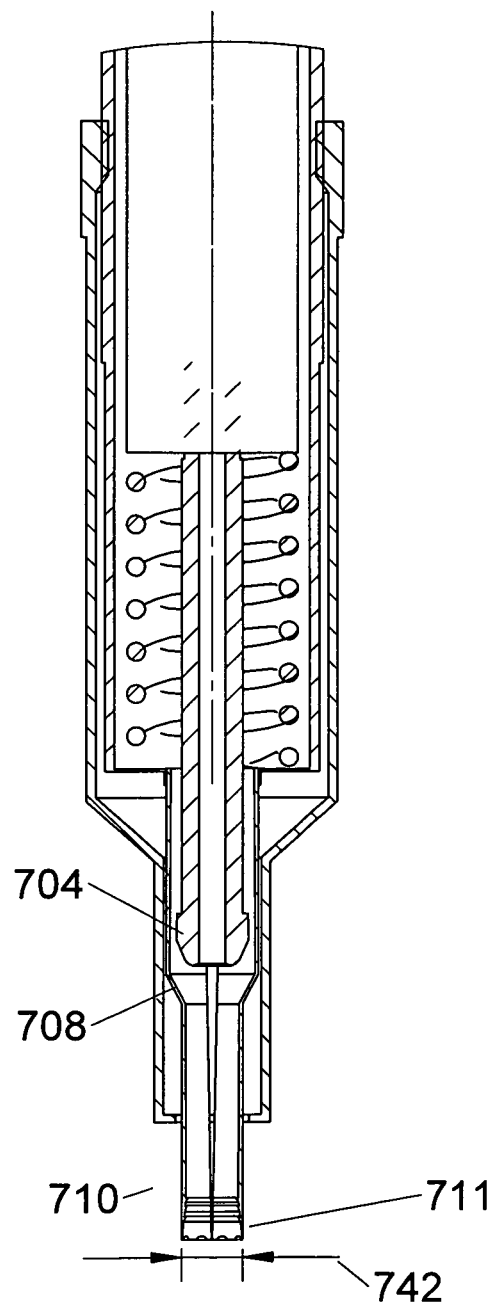
FIG. 7h is a diagram showing a partial assembly view of a punch in the closed position according to an embodiment.

FIG. 7h illustrates a particular embodiment of a punch 710. According to a particular embodiment, punch 710 may be in a collapsed position as mechanical member 704 is retracted into a particular position away from inclined surface 708. Members 711 may be in contact with one another giving punch 710 a particular inside diameter 742.

Figure 8:
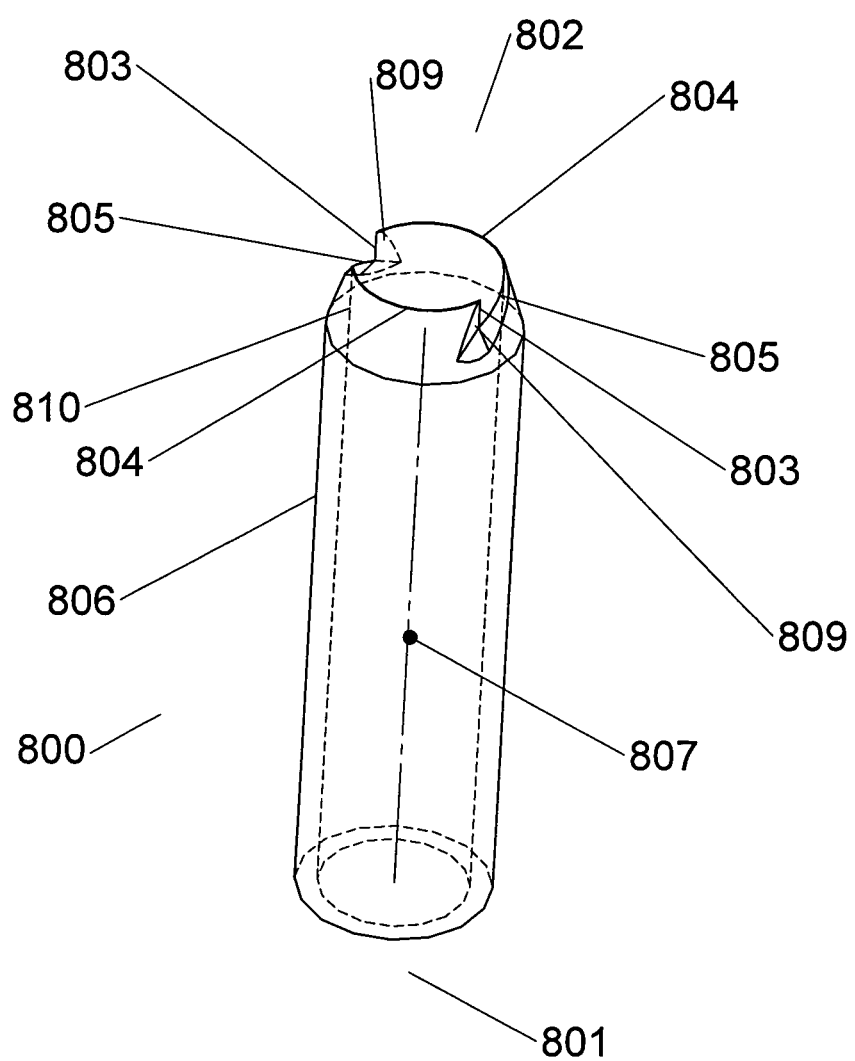
FIG. 8 is a diagram of a punch with cutting edges in the direction of the punch axis.

In FIG. 8, a particular embodiment of a punch 800 is illustrated. A punch 800 may have a first end 801 and a second end 802. Second end 802 may have one or more primary cutting edges 803, secondary cutting edges 804, lead-in grooves 805, primary relief faces 809 and secondary relief faces 810. In a particular embodiment, lead-in groove 805 may comprise a recess formed by primary cutting edge 803 and secondary cutting edge 804. According to a particular embodiment, a lead-in groove 805 may enable deformation of skin (not shown) into such a recess during a follicular dissection procedure. A relief face (such as primary relief face 809), is a surface behind a cutting edge (such as primary cutting edge 803). In a particular embodiment, primary cutting edges 803 may be angled with respect to longitudinal axis 807. According to a particular embodiment, secondary cutting edges 804 may be substantially perpendicular to punch axis 807. Also, lead-in grooves 805 may be angled with respect to longitudinal axis 807. Primary relief faces 809 may point in a clockwise or counterclockwise direction. According to a particular embodiment, primary cutting edges 803 may be located on a cylindrical surface 806 parallel to longitudinal axis 807. Secondary cutting edge 804 may be located on a peripheral edge of punch 800. Primary cutting edge 803 and secondary cutting edge 804 may vary from one another in many aspects depending on a particular function of punch 800. For instance, primary cutting edge may be sharp and secondary cutting edge may be dull or less sharp. Additionally, primary cutting edge may be serrated while secondary cutting edge may have a straight edge or vice versa. The sharpness may be characterized by an edge radius where a very sharp edge radius is close to zero. However, these are merely examples of ways in which to configure a punch having multiple cutting edges, grooves and relief faces and claimed subject matter is not limited in this regard.

In a particular embodiment, punch 800 may be pushed against the skin (not shown) of a patient allowing secondary cutting edges 804 to compress skin which may drive a portion of skin into lead-in groove 805 of primary cutting edge 803. When punch 800 is rotated in the direction of the primary cutting edge 803, primary cutting edge 803 may incise skin ahead of it with little force. According to a particular embodiment, punch 800 may be rotated and/or extended into the skin of a patient to a desired depth. Primary cutting edges 803 may perform the main incising action while secondary cutting edges 804 may be drawn along an already incised surface of the skin. In another embodiment, punch 810 may be extended into the skin of a patient without rotation after scoring has been made by rotating punch 800. In another embodiment, primary cutting edges 803 may not perform the incising action. Here, secondary cutting edges 804 may perform the incising action. If the secondary cutting edge 804 is rounded or is not as sharp as primary cutting edge 803, secondary cutting edge 804 may be capable of dissecting very soft tissue. Primary cutting edges 803 and secondary cutting edges 804, may take on a variety of configurations. Primary cutting edges 803 may be angled with respect to longitudinal axis 807 at various angles and may have sharp or radius corners. Secondary cutting edges 804 may be angled, straight, serrated, and/or may be sharp or dull. Lead-in grooves 805 may also have a variety of geometries and sizes.

In a particular embodiment, during a follicular dissection procedure, scoring and/or dissection may be achieved using punch 810. In one embodiment, dissection without scoring may be accomplished by rotating punch 810 in the direction of a primary cutting edge 803 (clockwise or counterclockwise) while pushing punch 800 to the desired depth in the skin. Alternatively, in another embodiment, scoring and dissection may be performed by first scoring and then dissecting a tissue sample. Scoring may be achieved by touching punch 800 to the surface of the skin of a patient and rotating punch 800 in the direction of primary cutting edge 803 (clockwise or counterclockwise). Dissection may then be performed by pushing punch 800 to the depth scored and extending punch 800 (either manually or mechanically) into the skin thus allowing tissue to be further cut with secondary cutting edges 804. In another embodiment, rotating punch 800 backward may enable dissection and also collection of the follicle or "splay." In this context, a "splay" comprises a follicular unit comprising more than one hair. The diameter of hair follicles, typically, is much smaller at the surface of the skin than under the surface of the skin. As the follicles enter the skin, they tend to spread out and the distance between the follicles increases. The divergence is called a splay. This action may reduce the risk of transecting follicular grafts (not shown). With the above described follicular dissection punch and method friction and torsional stress may be reduced between a punch and tissue. In this context, a torsional stress comprises a stress produced on the skin by a rotating motion or by force acting about a center of rotation. When punch 800 comes into contact with the skin and is rotated, the contact friction between the punch and the skin results in a circumferential force. This force tends to pull the skin in the direction of rotation creating a torsional effect. When the skin is twisted in this way, the graft to be dissected could be misplaced and may be subject to damage. The torsional effect on the graft may also cause the graft to coil on itself such that injury of the hair follicles may occur. Additionally, in this context, friction is produced between a moving punch and the skin. There may be friction in the circumferential direction due to a rotation of punch 800 and in the axial direction due to insertion of punch 800 into the skin. If friction forces are high, higher dissection forces are applied that may bend, bury or otherwise damage a graft. Another effect of friction is to dull the cutting edges. However, these are merely examples of ways in which to perform a follicular dissection and claimed subject matter is not limited in this respect.

Figure 9A:
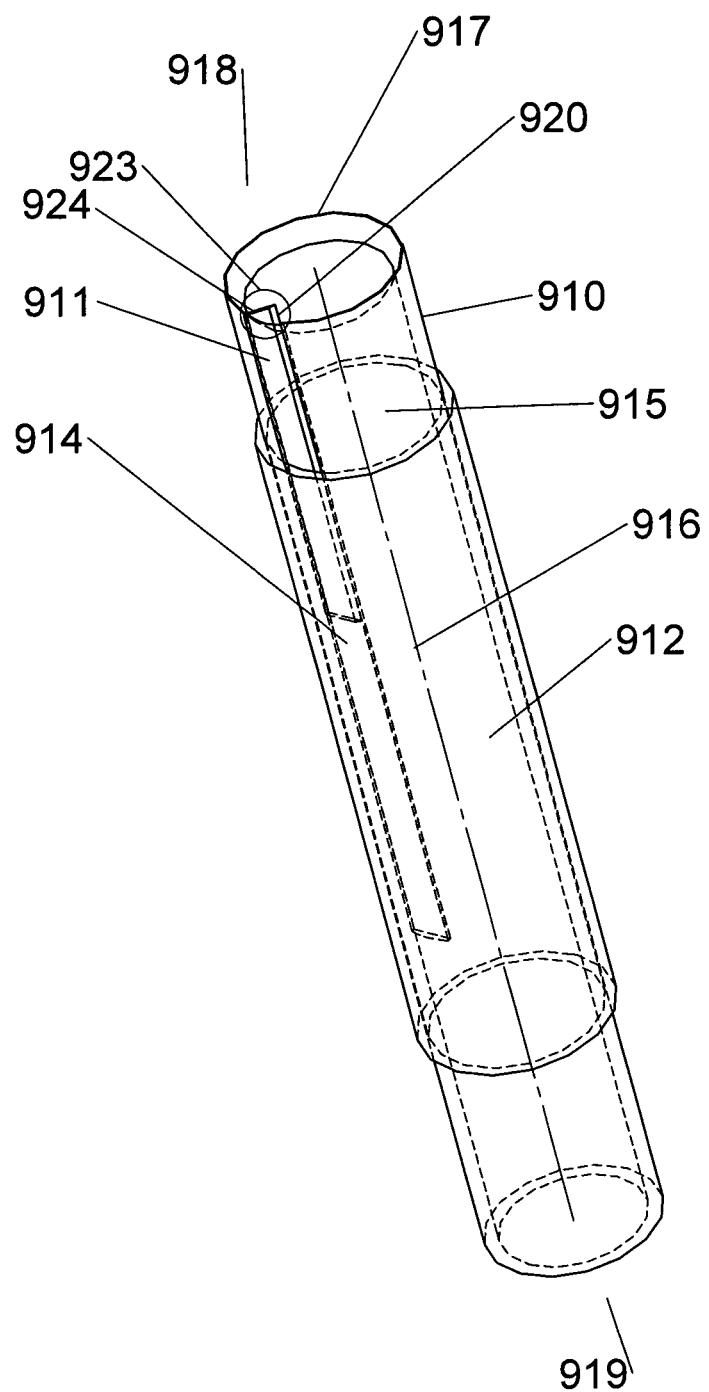
FIG. 9a is a diagram of a punch with sliding cutting blade.
Figure 9B:
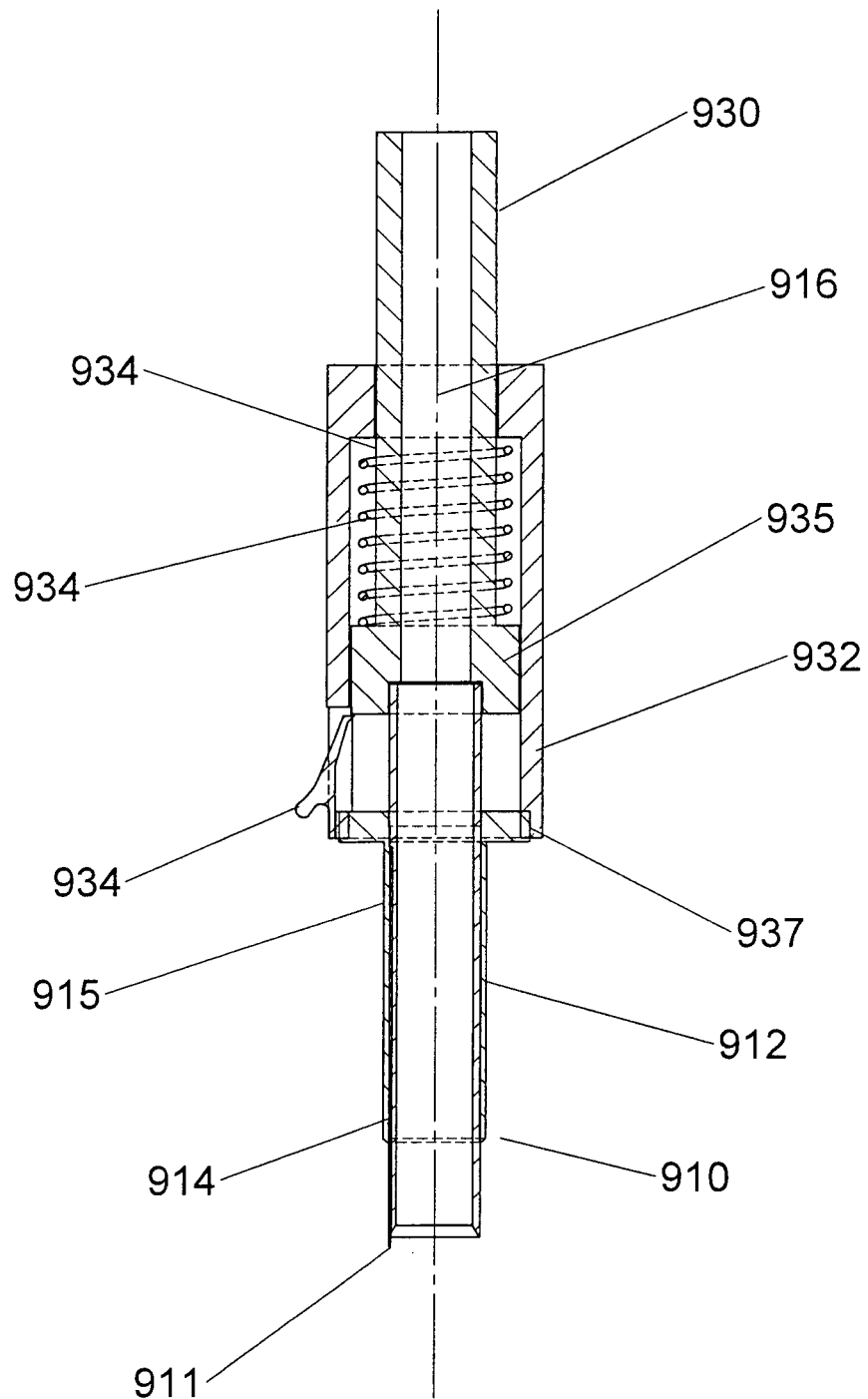
FIG. 9b is a diagram showing a partial assembly of a punch with sliding cutting blade.

FIGS. 9a-9c illustrate various perspectives of a punch 910. FIG. 9a, illustrates a particular embodiment of a punch 910. In a particular embodiment, punch 910 may be coupled to at least one sliding blade 911 and a sliding blade holder 912. Punch 910 may be cylindrically shaped having at least one axial groove 914 on cylindrical surface 915. In a particular embodiment, blade holder 912 may be substantially cylindrical and positioned concentrically to cylindrical surface 915 of punch 910. Sliding blade 911 may be coupled to axial groove 914 and blade holder 912. In a particular embodiment, sliding blade 911 may be extended and protracted in the direction of the longitudinal axis 916 by translational motion of blade holder 912. However, this is merely an example of a particular embodiment of a punch having a sliding blade. There are many ways in which to couple a sliding blade to a punch and claimed subject matter is not limited in this regard.

In a particular embodiment, punch 910 may have a first end 918 and a second end 919 and may have a secondary cutting edge 917 located at first end 918. Secondary cutting edge 917 may be sharp or dull and may have a variety of edge configurations such as, for instance, denticulated, serrated and/or straight. Sliding blade 911 may have a primary cutting edge 920. Primary cutting edge 920 may be positioned at first end 918 and may be sharp or dull and may have a variety of edge configurations such as, for instance, denticulated, serrated and/or straight. In a particular embodiment, primary cutting edge 920 may protrude beyond secondary cutting edge 917. Accordingly, a portion of sliding blade 911 extending beyond secondary cutting edge is depicted in FIG. 9a as extended portion 923 of sliding blade 911. In a particular embodiment, primary cutting edge 920 may have a face oriented in any direction with respect to punch 910, such as, for instance, pointing in the clockwise or counterclockwise direction. During a follicular dissection procedure, the direction faced by primary cutting edge 920 may determine the direction of rotation of punch 910 in order to make an incision into the skin. Additionally, back edge 924 of sliding blade 911 may be angled with respect to the plane containing edge 917. In a particular embodiment, sliding blade 911 may extend beyond secondary cutting edge 917 a fixed amount which may be between 0.1 mm and 2.5 mm. In a particular embodiment, sliding blade 911 may be fixedly coupled to blade holder 912 by a mechanical means, molding-in, gluing or any appropriate means. However, these are merely examples of edges and orientations of primary and secondary cutting edges and ways in which a punch blade may be coupled to a blade holder and claimed subject matter is not limited in this regard.

In a particular embodiment, punch 910 may enable scoring of skin during a follicular dissection procedure. A user may extend sliding blade 911 to a desired length and then with punch 910 contact the surface of the skin to be scored, rotating and inserting punch 910 to the scoring depth desired. Dissection may follow scoring by inserting punch 910 deeper into the tissue of the skin using secondary cutting edge 917. Alternatively, dissection only may be accomplished by pushing punch 910 into the skin and also oscillating or rotating the punch. The risk of transecting grafts may be reduced here by retracting sliding blade 911 after scoring and allowing the secondary cutting edge 917 to collect the splay (not shown). Punch 910 may be coupled to a PFID (not shown) in order to induce a rotary motion. In a particular embodiment, a cutting action using punch 910 during a follicular dissection procedure may be facilitated by the oscillating, rotating and/or translating motion transferred to punch 910 by a PFID. However, these are merely examples of methods of scoring and dissecting tissue and coupling a punch to a PFID device, and claimed subject matter is not limited in this regard.

The deformation and twisting of the skin during a follicular dissection procedure may be reduced with punch 910. Typically, during a dissection procedure where an incision is made by rotation of a sharp edge against the skin of the patient, friction force between the sharp edge and the skin may result in twisting or deformation of the skin. However, punch 910 may have a cutting edge facing the direction of rotation, thus the skin may be incised rather than being pulled or dragged by punch 910. In a particular embodiment, primary cutting edge 920 may face the direction of rotation of punch 910 during an incision and thus may introduce only a small force on the skin reducing deformation of the skin.

FIG. 9b illustrates a particular embodiment of punch 910 capable of holding the position of sliding blade 911. According to a particular embodiment, punch 910 may be coupled to a sliding blade 911 which may reside in an axial groove 914 on a cylindrical surface 915 of punch 910, as described above. In a particular embodiment, punch 910 may be coupled to punch holder 930. Punch holder 930 may be substantially hollow and may support a spring 933 with a support collar 935. Spring 933 may reside about the outside surface 936 of punch holder 930. Blade holder 912 may be coupled to punch holder 930. Spring 936 may be loaded between punch holder 930 and blade holder 912. Spring 936 may push blade holder 912 and extend sliding blade 911. However, these are merely examples of ways in which a punch may be coupled to a sliding blade and spring and subject matter is not limited in this regard. In a particular embodiment sliding blade 911 may be locked in position by a mechanical lock 934. When blade holder 912 is extended a mechanical lock 934 may latch against support collar 935 on punch holder 930 which may lock sliding blade 911 into position. Mechanical lock 934 may latch support collar 935 by a variety of methods such as, for instance, by a ratchet lock, by a pin connection, cam lock, by friction, and or magnetic lock. Sliding blade 911 may be retracted by releasing mechanical lock 934. When mechanical lock 934 is released, spring 936 may be activated to push back on blade holder 912. Sliding blade 911 may be moved axially by securing a position of punch 910 with punch holder 930 and moving a sliding blade 911 into position relative to punch 910. Spring box 932 which may be coupled to blade holder 912 by threading 937 and may be moved manually in order to reposition sliding blade 911 with respect to punch 910. However, these are merely examples of ways in which a mechanical lock may operate against a support collar and claimed subject matter is not limited in this regard.

FIG. 10*a*-FIG. 10*i*, depict different mechanisms to control a punch dissection depth. A variety of fixed and variable depth stops are demonstrated. These depth stops may be used interchangeably with any of a variety of punches such as, for instance, cylindrical punches having uniform diameter, stepped punches with variable diameters and/or any of the above described punches. Description of various depth stops is meant to be illustrative and claimed subject matter is not limited to the particular embodiments described herein.

FIG. 10*a* illustrates a depth marker 1000 that may be applied to an outside surface of any punch as described above. In a particular embodiment, marker points 1001 may be applied by a variety of methods, such as, for instance, by printing, laser marking, etching, label application, stamping, and/or scribing. Marker points 1001 may be applied at specified distances such as 0.1 mm, 0.25 mm, 0.5 mm or 1 mm or more apart. In a particular embodiment, depth marker 1001 may be applied to a punch 1002. Punch 1002 may be inserted into the skin (not shown) and the depth of insertion may be observed. When the desired depth marker 1001 is aligned with the skin (not shown) the user may physically stop inserting punch 1002 further into the tissue.

FIG. 10*b* illustrates a color depth marker 1003 applied to a punch. A variety of different color markings 1006 may be applied to surface 1004 of punch 1005 at specified distances such as 0.5 mm or 1 mm apart. Punch 1005 may be inserted into the skin (not shown) and the depth may be observed as a color marking 1006 indicating a desired depth is aligned with the skin (not shown). When the desired depth is reached the user may physically stop inserting punch 1005 into the skin. As described above, the markings may be done by printing, laser marking, anodizing, etching, label application, stamping, scribing, or any similar method.

FIG. 10*c* illustrates a depth marker 1007 and sliding ring 1008 that may be applied to an outside surface of any punch as described above. In a particular embodiment, marker points 1009 may be applied to a surface of a punch 1010 as described above with reference to FIGS. 10*a* and 10*b*. In a particular embodiment, at least one sliding ring 1008 may be coupled to punch 1010 and may be movable in an axial direction. One end of sliding ring 1008 may be aligned to a desired marker point 1009 and may be fixed in position by using fasteners, such as, for instance, set screws, threading, friction lock, and/or snug sliding fit. Punch 1010 may be inserted into the skin (not shown) and the depth may be observed and physically indicated as sliding ring 1008 comes into contact with the skin when a desired depth is reached and prevents further insertion of punch 1010 into the skin.

FIG. 10*d* illustrates a depth marker shoulder 1011 coupled to a punch 1012. The dissection depth may be the length between cutting tip 1013 and depth marker shoulder 1011. Depth marker 1011 may be fixed in position during manufacturing of punch 1012. When punch 1012 may be inserted into the skin (not shown) during a follicular dissection procedure when the depth marker shoulder 1011 comes into contact with the skin, the user may manually stop inserting punch 1012 into the skin. Alternatively, the diameter of the punch 1012 may be greater than the diameter of depth marker 1011. In such a case, when the desired depth is reached, depth marker shoulder 1011 may prevent insertion of punch 1012 beyond a desired insertion depth. Depth marker shoulder 1011 may be made by a variety of methods, such as, for instance, metal forming, machining processes or electrochemical machining process.

FIG. 10*e* illustrates a depth marker groove 1014 coupled to a punch 1015. In a particular embodiment, punch 1015 may have at least one depth marker groove 1014 cut circumferentially about the cylindrical surface of punch 1015. The dissection depth may be the length between the cutting tip 1016 of punch 1015 and depth marker groove 1014. In a particular embodiment, punch 1015 may be inserted into the skin (not shown) as far as the edge of the depth marker groove 1014. Upon reaching depth marker groove 1014, punch 1015 may be prevented from being inserted further into the skin of a patient during a follicular dissection procedure. Depth marker groove 1014 may be manufactured into punch 1015 by a variety of methods, such as, for instance, metal forming, machining processes or electrochemical machining process during manufacturing.

FIG. 10*f* illustrates an embodiment of a depth marker 1018 with sliding handle 1017 coupled to a punch 1016. Marker scale points 1019 are applied to the outside surface of the punch 1016 at specified distances such as 0.1 mm, 0.25 mm, 0.5 mm or 1 mm apart. Sliding handle 1017 may be made concentric to a punch 1016 and may be moved up and down with respect to a longitudinal axis 1020. Sliding handle 1017 may be moved to a particular depth and may be fixed in position by using fasteners like set screws, friction lock, threading and/or similar techniques.

FIG. 10*g* illustrates an embodiment of a depth marker 1021 with sliding scale 1022 coupled to a punch 1023. When punch 1023 is inserted into the skin (not shown), sliding scale 1022 may be pushed back into handle 1020. A reference edge 1028 on punch 1023 may be aligned to markings on scale 1029. The markings on scale 1029 may be made by printing, etching, label application, stamping, scribing, or any similar method.

FIG. 10*h* illustrates a depth marker 1027 with a sliding handle 1025 having scale viewing window 1024. The viewing window 1024 may also contain a magnifying lens (not shown). The marker scale points (not shown) are applied to the outside surface of punch 1026 at specified distances such as 0.1 mm, 0.25 mm, 0.5 mm or 1 mm apart. Sliding handle 1025 may be positioned concentric to punch 1026 and may be extendable and/or retractable. Marker scale points (not shown) on punch 1026 outside surface may be viewed through viewing window 1024 on sliding handle 1025. Sliding handle 1025 may be moved to a particular depth and may be fixed in position by using fasteners like set screws, friction lock, threading and similar techniques.

FIG. 10*i* illustrates a depth stop 1037 with a sliding ring collar 1038 and handle 1035 on a barrel 1037. In a particular embodiment, a depth control assembly comprises a barrel 1037 with shoulder 1030 and threading (not shown), a depth adjust nut 1032 and a counter nut 1039 threaded to punch holding screw 1031, a sliding ring collar 1038 that may slide between depth adjust nut 1032 and barrel shoulder 1030. Marker scale 1033 points may be applied to an outside surface of barrel 1037 at specified distances, such as, for instance, 0.1 mm, 0.25 mm, 0.5 mm or 1 mm apart. In a particular embodiment, punch 1034 and barrel tip 1036 may be set at a certain distance by threading (not shown) punch holding screw 1031 into barrel 1037 and locking it in position against the barrel top surface (not shown) with counter-nut 1039. A sliding ring collar 1038 attached to handle 1035 may be disposed concentrically to barrel 1037. Barrel 1037 may have a barrel shoulder stop 1030 and may be coupled to an adjustable nut 1032. In a particular embodiment, sliding ring collar 1038 may freely move between barrel shoulder 1030 and nut 1032. Nut 1032 may be rotated to push sliding ring collar 1039 to a certain position to fix the dissection depth. According to a particular embodiment, punch 1034 may touch the skin surface (not shown) while a user holds the handle with the collar against the nut 1032 at a fixed position and pushes punch 1034 into the skin until the shoulder 1030 hits against the collar.

However, the above descriptions of depth stops are merely examples of ways in which a punch may be coupled to a depth stop or depth indicator and claimed subject matter is not so limited.

FIGS. 11-15 illustrate various embodiments of a Powered Follicular Isolation Device (PFID) that may be coupled to any of the punches described in the current disclosure. In general a PFID may be any of a variety of mechanized graft dissection devices capable of imparting motion to a punch. Such motion may comprise, for instance, rotating, vibrating, oscillating, translating and/or vibrating motion. A PFID may be further capable of extending and retracting a punch along a longitudinal axis under controlled conditions such as rotational speed, punch advance rate or speed, and/or oscillation angle, etc.

In various embodiments coupling a PFID with a punch for use during a follicular dissection procedure may enable a reduction in skin bending, a reduction in torsional stress on the skin, reduced transection rates and may promote uniform dissection. Additionally, in particular embodiments, use of a PFID coupled to a punch may cause less fatigue on the user during a follicular dissection procedure than a manually operated punch. Use of a PFID may also increase dissection speed and enable an increased follicular extraction yield.

Figure 11A:
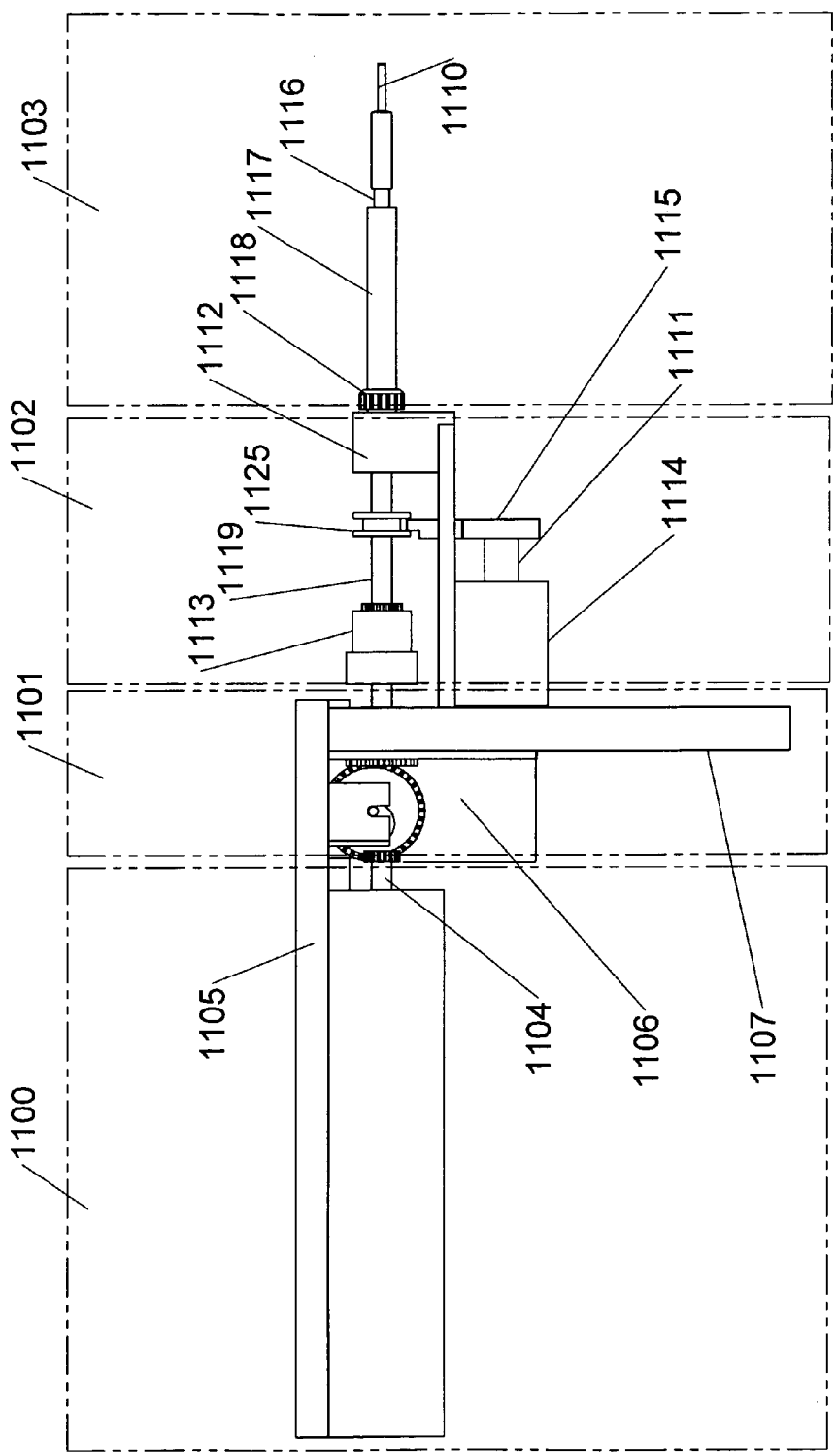
FIG. 11a is a diagram showing a layout of a Powered Follicular Isolation Device.

FIG. 11*a* illustrates a schematic of PFID 1108 comprising a solenoid actuated punch translation mechanism in four sections; a main drive section 1100, a motion conversion mechanism section 1101, a punch translation mechanism 1102, and a dissecting punch assembly 1103.

A main drive section 1100 may consist of a power source (not shown), a main motion source 1104, and housing 1105. In a particular embodiment, motion may be delivered by a variety of mechanisms, such as, for instance, by an electric motor, air motor, hydraulic motor, rotary solenoid and/or a stepped motor. In a particular embodiment, motion may be delivered in a variety of forms, such as, for instance, as rotary power at constant or variable speed and/or oscillating power at different angles.

A motion conversion mechanism section 1101 may enable conversion of rotary motion to a variety of other motions, such as, for instance, oscillating, vibrating and/or reciprocating motion. Motion conversion mechanism section 1101 may comprise a housing 1106, a handle 1107, a solenoid 1114 and switches (not shown). In a particular embodiment, a motion conversion mechanism may be any of a variety of conversion mechanisms, such as, for instance, rotary to rotary at a different speed, rotary to oscillating and/or rotary to reciprocating. Motion conversion component parts may comprise discs, linkages, cams, pins, and/or gear assemblies (such as, for instance, a bevel, rack and pinion and/or spline). Output may be any of a variety of motions, such as, for instance, rotating, oscillating, reciprocating or vibrating or a combination thereof. Rotation of a punch 1110 when coupled to PFID 1108 may range from 30 rpm to 30,000 rpm. Oscillation of the punch may be any angle between 5 deg to 360 degrees. Reciprocating or vibrating motion may be 60 to 30,000 strokes per min. Higher stroke rates may be obtained by using sonic and ultrasonic vibration sources.

In a particular embodiment, punch movement system 1102 may enable a user to extend, retract, and/or cause a reciprocating motion of a punch 1110 during a follicular dissection procedure. In a particular embodiment, a punch 1110 coupled to PFID 1108 may be extended and/or retracted by a linear solenoid actuator 1111 and spring return (not shown) mechanism during a follicular dissection procedure. In another particular embodiment, solenoid 1114 may activate linear solenoid actuator 1111 which in turn may extend or retract punch 1110 via fork 1115. Fork 1115 may be moved back and forth and may be coupled to a collar 1125 fixed to an output shaft 1119. Fork 1115 may push or pull collar 1125. Collar 1125 may move shaft and punch 1110 accordingly. Other mechanisms for moving a punch 1110 coupled to PFID 1108 may be used such as, for instance, by manually moving PFID 1108, by activation of a mechanical trigger with a manual punch advance and a spring return, by a spring loaded punch advance and manual return, by a combination of solenoid actuators for a multiple position punch advance, by a pneumatic actuator for the punch advance and punch return, by a hydraulic actuator for the punch advance and punch return, with a motorized lead screw and nut assembly for axial movements, with step motors having an electronic controller, by a cam drive system, or any combination of the foregoing. However, these are merely examples of methods of moving a punch coupled to a PFID and translating motion to a punch and claimed subject matter is not limited in this respect.

In a particular embodiment, a dissecting punch assembly 1103 may comprise a punch 1110, a punch holder 1116, a barrel (not shown), a hollow threaded shaft 1117, and counter nut 1118. In a particular embodiment, a punch 1110 may be fixedly coupled to punch holder 1116. Punch holder 1116 may be extended or retracted and may be fixedly coupled to a spline output shaft 1119. In a particular embodiment, dissecting punch assembly 1103 may slide back and forth in the axial direction, rotate, vibrate and/or oscillate. Punch holder 1116 may be supported by hollow threaded shaft 1117. Hollow threaded shaft 1117 may have a bearing surface (not shown) on the inside and a threaded connection (not shown) on the outside. Hollow threaded shaft 1117 may be connected to a bearing plate 1112 and fixed in position with a counter nut 1118. A barrel (not shown), which may act as a depth stop when punch 1110 is advanced into the skin of a patient, may be threaded to the outside of hollow shaft 1117 and fixed in position with a counter nut (not shown). However, these are merely examples of various configurations of a PFID and claimed subject matter is not so limited.

Figure 11B:
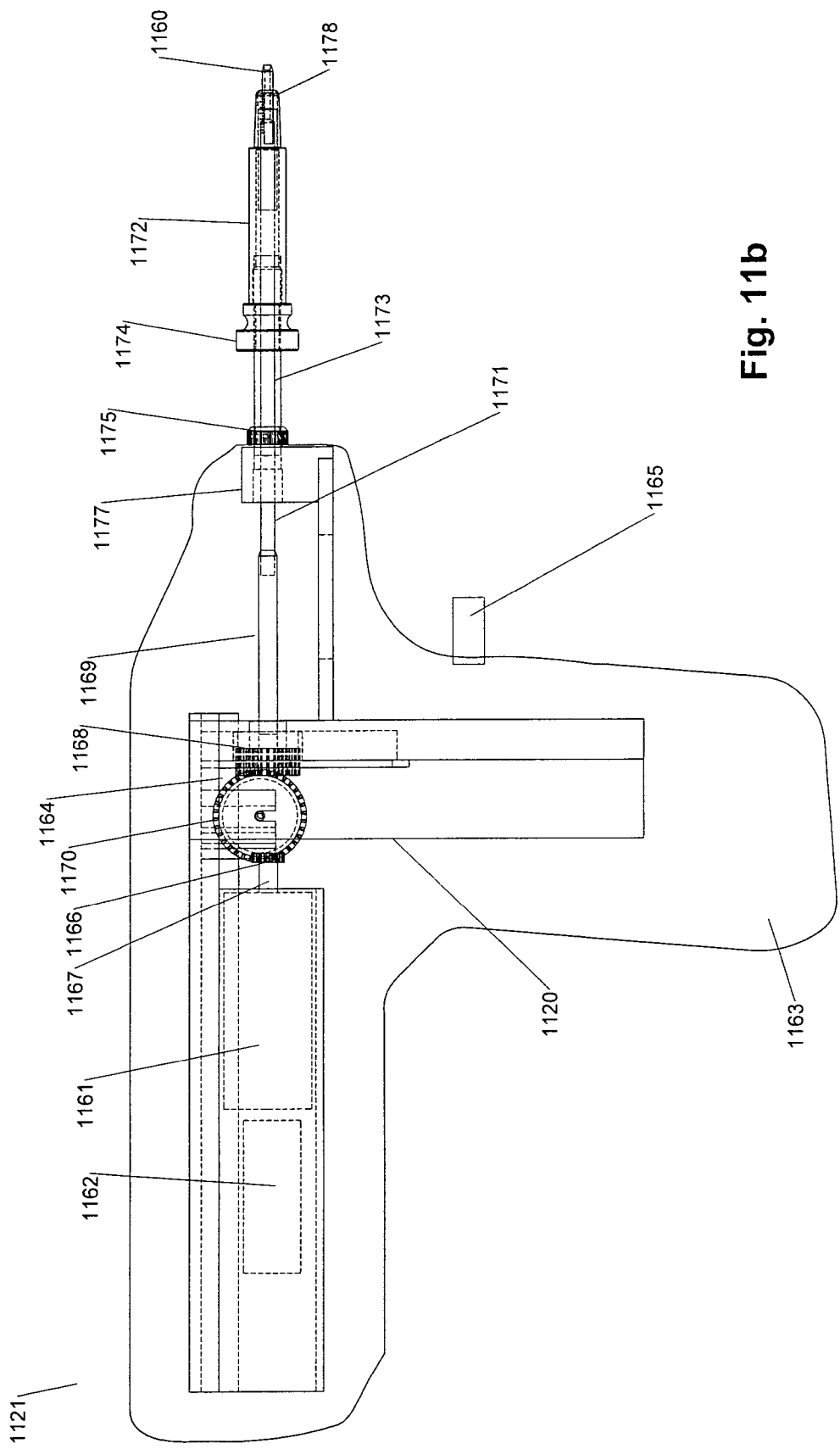
FIG. 11b is a diagram showing a Powered Follicular Isolation Device according to an embodiment.

FIG. 11*b* illustrates a particular embodiment of a punch 1160 coupled to PFID 1121. According to a particular embodiment, rotary motion at a certain speed may be delivered by an electromotor 1161 and may be powered by a battery 1162. Rotary motion delivered by electromotor 1161 at a certain speed may be transferred to punch 1160 directly. In a particular embodiment, rotary motion obtained from electromotor 1161 at a particular speed may be converted to a rotary motion at a different speed. A motion conversion mechanism section 1120 may enable conversion of rotary motion at a given speed to a rotary motion at a different speed. Motion conversion mechanism section 1120 may comprise a housing 1163, a gear set 1164, and switch 1165. In a particular embodiment, the mechanism consists of a combination of a set of gears used to change the rotational speed to another speed delivered to punch 1160. Gear set 1164 may comprise a pinion bevel gear 1166 connected to the motor shaft 1167, an output bevel gear 1168 connected to the output shaft 1169, a driven bevel gear 1170 connected between the pinion bevel gear 1166 and the output bevel gear 1168. Rotation of a punch 1160 when coupled to PFID 1121 may range from 30 rpm to 30,000 rpm. However, this is merely an example of ways in which a gear set may be designed for motion conversion. It should be understood that such a gear set may be designed from a variety of combinations of gears, cams and linkages and claimed subject matter is not limited in this regard.

In a particular embodiment shown in FIG. 11*b*, a dissecting punch 1160 assembly may comprise a punch 1160, a punch holder 1171, a barrel 1172, a hollow screw 1173, a first counter nut 1174 and a second counter nut 1175. In a particular embodiment, a punch 1160 may be coupled to punch holder 1171. Punch holder 1171 may be coupled to output shaft 1169 and may be supported by hollow screw 1173. Hollow screw 1173 may have a bearing surface on the inside and a threaded connection on the outside shown by the double line. Hollow shaft 1173 may be connected to a bearing plate 1177 and fixed in position with second counter nut 1175. Barrel 1172 may be coupled to the outside of hollow screw 1173 and fixed in position with a first counter nut 1174. Such an assembly allows a free rotation of the punch 1160 within barrel 1172.

There are a variety of ways for moving a punch 1160 coupled to PFID 1121 to the dissecting position and perform the dissection procedure. Referring to FIG. 11*b* for instance, punch 1160 advance movement may be performed by manually moving PFID 1121. According to a particular embodiment, rotating punch 1160 may be aligned to the hair follicle (not shown) and PFID 1121 may be pushed forward inserting punch 1160 into the skin (not shown) until the depth stop 1178 at the tip of barrel 1172 touches the skin. Punch 1160 may then be withdrawn. However, this is merely an example of a punch coupled to a PFID capable of converting rotational motion at one speed to rotational motion at a different speed and claimed subject matter is not limited in this regard.

Figure 11C:
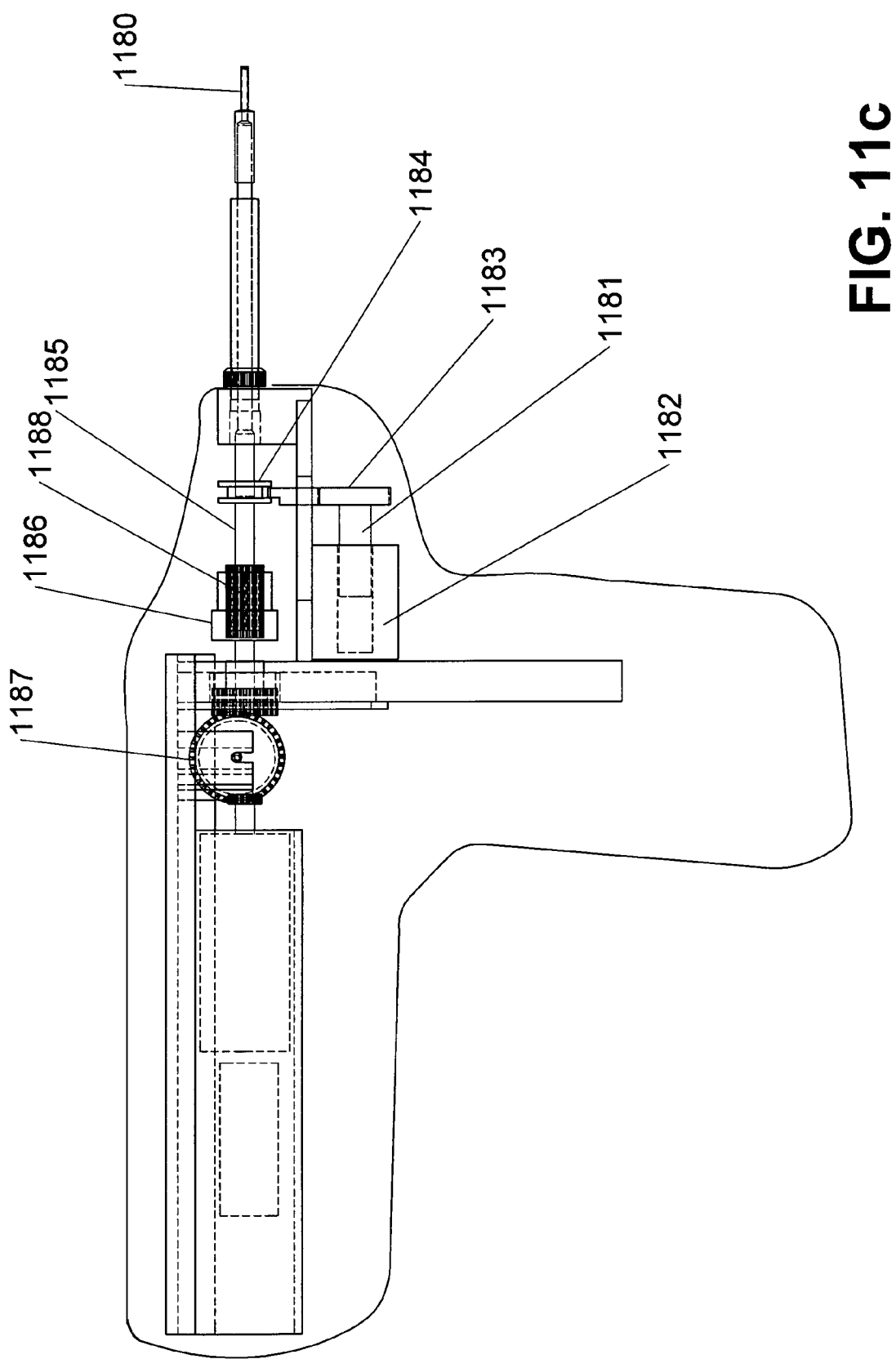
FIG. 11c is a diagram showing a Powered Follicular Isolation Device according to an embodiment.

In a particular embodiment shown in FIG. 11*c*, a punch translation mechanism may enable a user to extend, retract or cause a reciprocating motion of a punch 1180 during a follicular dissection procedure. In a particular embodiment, a punch 1180 coupled to PFID 1130 may be moved, such as extending and/or retracting, by a linear solenoid actuator 1181 and spring return mechanism (inside the solenoid) during a follicular dissection procedure. In a particular embodiment, solenoid 1182 may activate linear solenoid actuator 1181 which may extend or retract punch 1180 via fork 1183. Fork 1183 may be slidably coupled to collar 1184 while collar 1184 may be coupled to the output shaft 1185. Fork 1183 may push or pull collar 1184 which in turn may move output shaft 1185 coupled to the punch 1180. As described in FIG. 11*b*, the sliding of an output shaft 1185 may be performed by a spline internal gear 1186 coupled to output gear 1187. A sliding action may be performed with an external spline shaft 1188, shown inside spline internal gear 1186, that may be slidably geared into the internal spline. Alternatively, such a coupling may also be achieved by a sliding gear assembly or a shaft coupling using key or pin (not shown). The depth to which a punch 1180 may be inserted into skin of a patient may be controlled by adjusting the solenoid actuator stroke. Alternatively, punch depth adjustment, punch depth stop and/or punch return may also be provided as part of this mechanism. Such a mechanism is shown in further detail in FIG. 14.

Figure 11D:
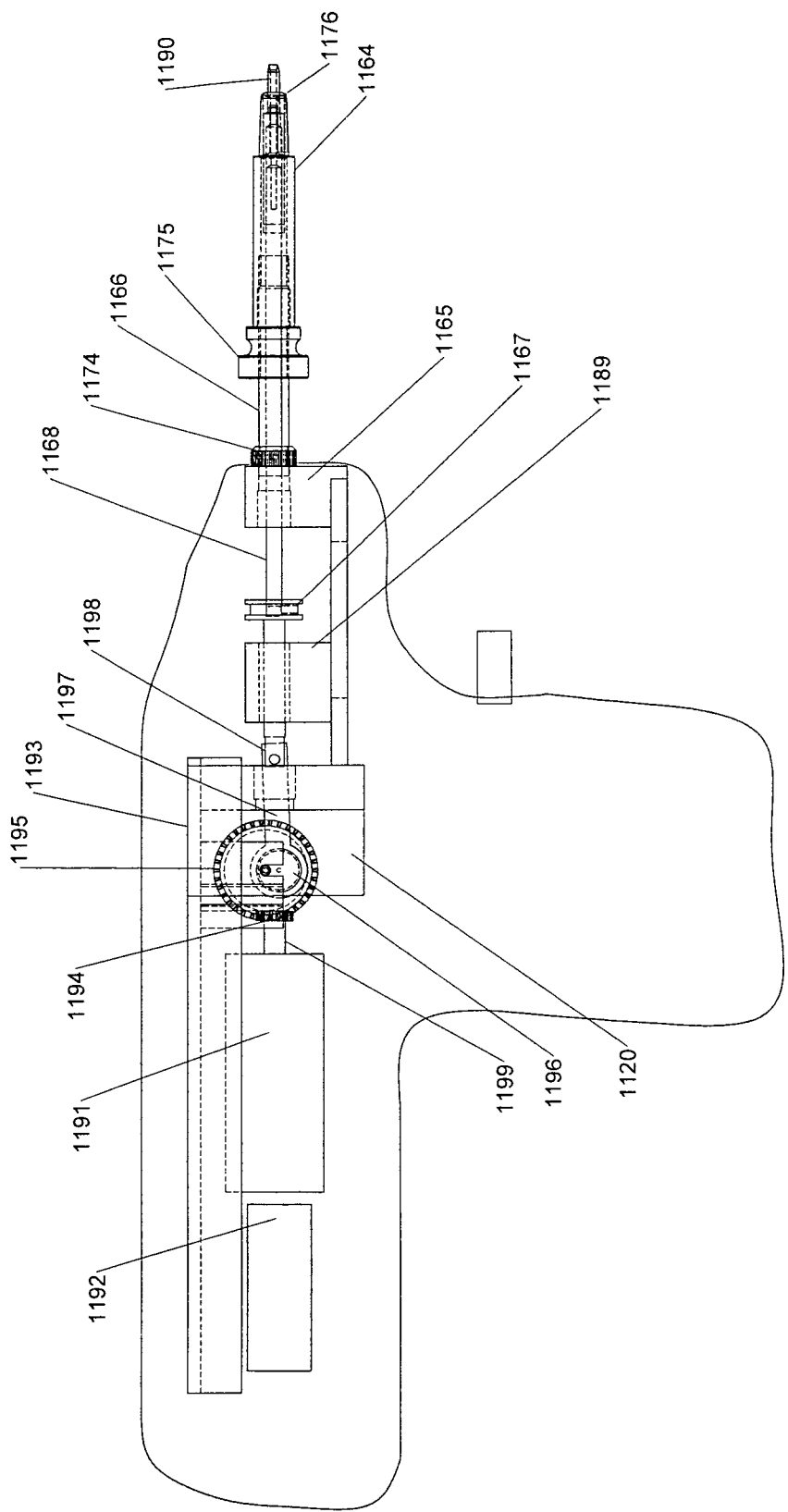
FIG. 11d is a diagram showing a Powered Follicular Isolation Device according to an embodiment.

FIG. 11*d* illustrates particular embodiment of a PFID 1140 having punch 1190 capable of reciprocating or vibrating along a punch axis at a certain number of strokes per minute. As discussed with reference to FIG. 11*c*, a rotary motion at a certain speed may be delivered by electromotor 1191 and may be powered by a power source like a battery 1192, for instance 30 rpm to 30,000 rpm. According to a particular embodiment, a motion conversion mechanism section 1120 may enable conversion of rotary motion at a given speed to a reciprocating motion at a certain number of strokes per minute. Motion conversion mechanism section 1120 may comprise a housing 1193, a pinion gear 1194, a driven gear 1195, a cam or offset disc 1196, a connecting rod 1197, a pin (not shown) and a reciprocating member 1198.

In a particular embodiment, the rotational motion from the motor shaft 1199 may be converted to a rotational motion at a different speed and then converted to a linear motion by a set of gears. Here, a cam 1196 may be connected to driven gear 1195 with a pin at the center of driven gear 1195. The center of cam 1196 may be located in the center of one end of connecting rod 1197 and may be offset from the center of driven gear 1195. Here the offset distance (not shown) determines the stroke length (not shown) of punch 1190. Additionally, reciprocating speed may be varied. According to a particular embodiment, connecting rod 1197 may be slidably connected to cam 1196 and may be constrained to reciprocate at the other end. Reciprocating member 1198 may be pin-connected to connecting rod 1197 and may be constrained to slide back and forth in guide 1189. A number of strokes per minute of punch 1190 may be determined by the rotational speed of motor 1191 and the gear ratio between pinion gear 1194 and driven gear 1195. A gear set design to make such motion conversion may be configured in a variety of different ways using different numbers, forms and combinations of gears. The reciprocating motion of a punch 1190 when coupled to a PFID may range from 30 strokes per minute (spm) to 40,000 spm.

In a particular embodiment, a punch 1190 may be fixedly coupled to punch holder 1168. Punch holder 1168 may be fixedly coupled to a reciprocating rod 1197 by a coupler 1167. The reciprocating member 1197 reciprocates punch holder 1168 and in turn punch 1190. Hollow screw 1166 may have a bearing surface on the inside and a threaded connection on the outside. Hollow screw 1166 may be connected to a bearing plate 1165 by threading and fixed in position with a first counter nut 1174. A barrel 1164 may determine punch 1190 depth and may be threaded to the outside of hollow screw 1166 and fixed in position with a second counter nut 1175. Such an assembly allows a free reciprocation of punch 1190 within the barrel.

Referring to FIG. 11*d*, punch advance movement may be performed by manually moving PFID 1140. The reciprocating punch may be aligned to the hair and the device may be pushed forward into the skin until the depth stop 1176 at the tip of the barrel 1164 touches the skin. Punch 1190 may then be withdrawn. However, it should be understood that the punch reciprocating mechanism given here is just an example. The reciprocating or vibrating motion may be generated by any other electromechanical, mechanical, sonic or ultrasonic means.

Figure 12:
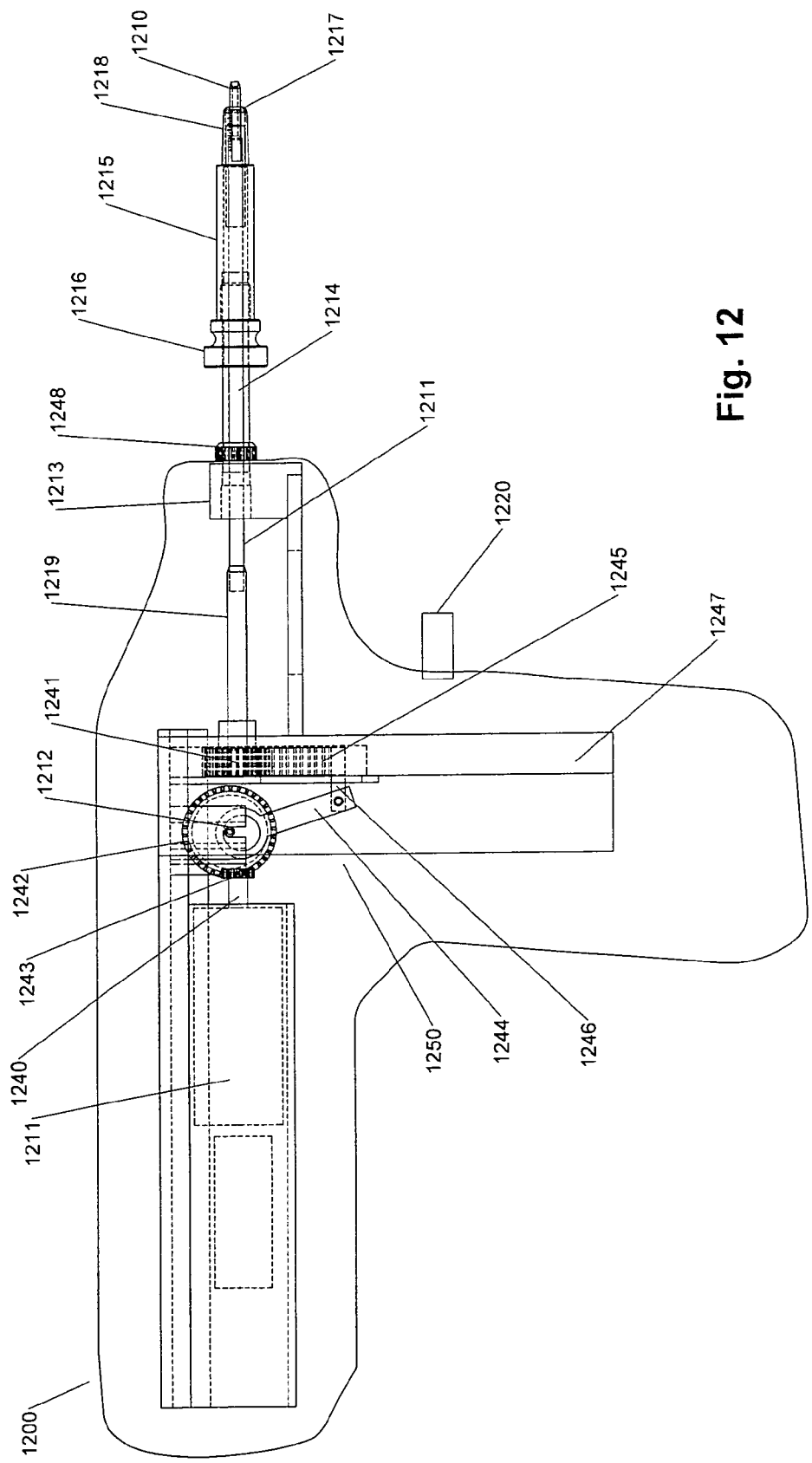
FIG. 12 is a diagram showing a Powered Follicular Isolation Device comprising a manual punch translation mechanism according to an embodiment.

FIG. 12 illustrates a particular embodiment of a punch 1210 coupled to a PFID 1200 comprising a manual punch translation mechanism. According to a particular embodiment, electric motor 1211 may generate rotational motion that may be converted to oscillating motion by a rack and pinion mechanism 1250. A motor shaft 1240 may be connected to a pinion output gear 1241 by means of the motion conversion mechanism. In a particular embodiment, driven gear 1242 may change the direction of rotation from clockwise or counterclockwise about the axis of the motor to a rotary motion about an axis perpendicular to that of the motor shaft axis and may also calibrate the speed to a desired rotational speed. An offset cam 1212 may be coupled to driven gear 1242 and may drive a connecting rod or plate 1244. Connecting rod 1244 may be coupled to a gear rack 1245 by a pin 1246. Gear rack 1245 may be driven by connecting rod 1244, and may be able to slide back and forth within housing 1247 in a vertical direction. Gear rack 1245 may drive a pinion output gear 1241 to oscillate as a result of a reciprocating action of gear rack 1245. Pinion output gear 1241 may be coupled to an output shaft 1219. Output shaft 1219 may be coupled to a punch holder 1211. Punch holder 1211 may pass through a bearing block 1213 and a hollow threaded shaft 1214. Hollow threaded shaft 1214 may be threaded to bearing block 1213 and be fixed in position by a counter nut 1248. A barrel 1215 assembly may be coupled to hollow threaded shaft 1214 by threading. The depth of punch 1210 may be adjusted by moving barrel 1215 axially on hollow screw 1214. Barrel 1215 may then be fixed in a position with a counter nut 1216. A switch 1220 may be activated that may start punch 1210 oscillating. Such an assembly allows a free oscillation of punch 1210 within barrel 1215. To make a dissection, punch 1210 may be centered over a hair (not shown) and aligned to the hair angle (not shown). A follicular dissection may be performed by moving PFID 1200 unit coupled to punch 1210 forward until punch 1210 is in position to dissect the follicle. Punch 1210 may be prevented from entering the skin of a patient beyond a desired depth when depth stop 1217 at barrel tip 1218 comes in contact with the skin surface (not shown). Punch 1210 may oscillate up to 360 degrees. Punch 1210 oscillation rate may be about 30 to 30,000 strokes per minute. The oscillation angle and rate may also be higher or lower than the indicated values. It should be understood that the foregoing is merely an example of a method of transferring and converting rotational motion from PFID 1200 to a punch using a mechanized system and of controlling the depth of a punch. As mentioned in FIG. 11 there are a variety of methods of translating motion through a device and claimed subject matter is not limited in this regard.

Figure 13:
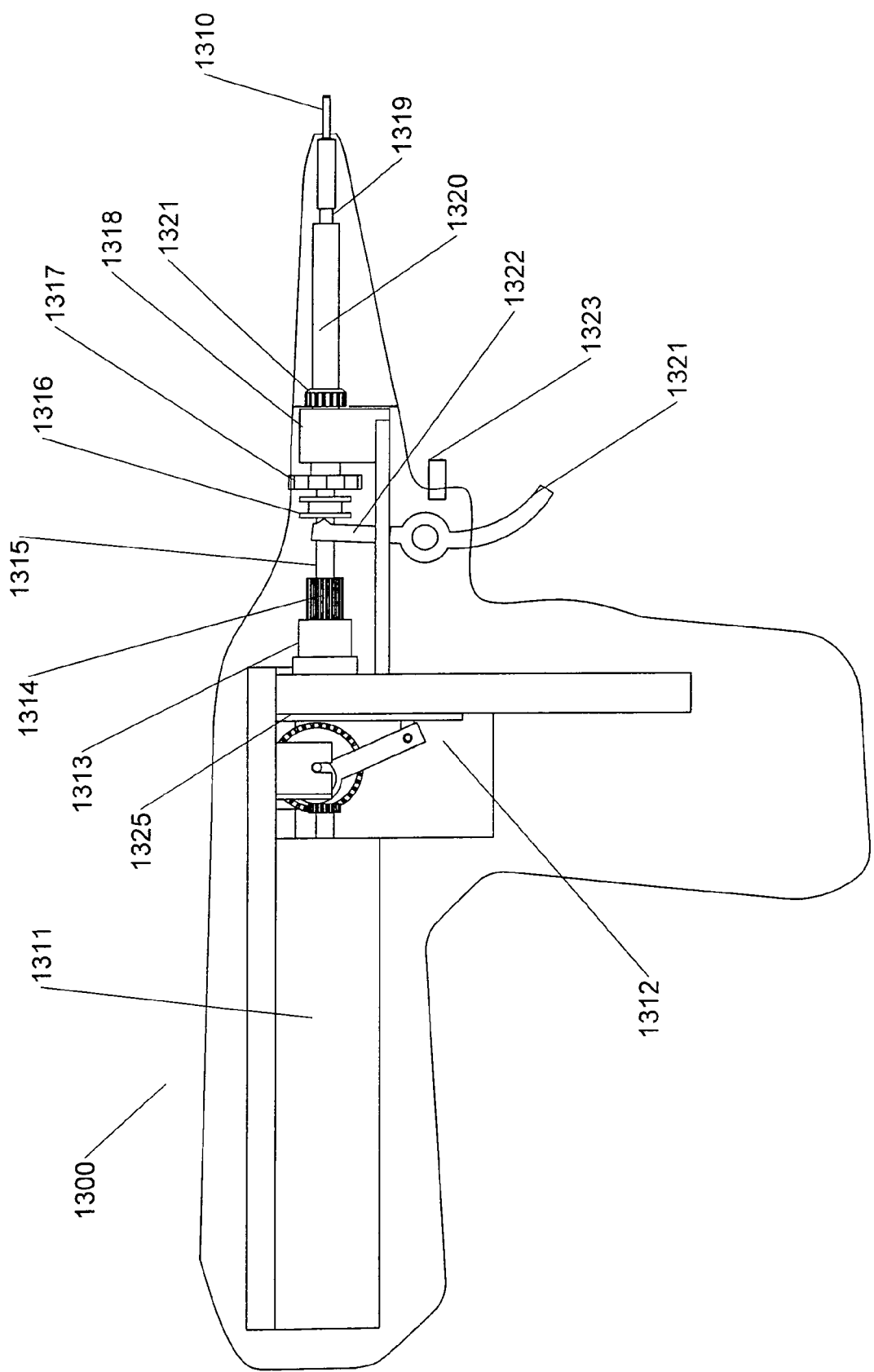
FIG. 13 is a diagram showing a Powered Follicular Isolation Device comprising a trigger punch translation mechanism according to an embodiment.

FIG. 13 illustrates another embodiment of a punch 1310 coupled to a PFID 1300 comprising a trigger punch translation mechanism. In a particular embodiment, an electric motor 1311 may be the source of motion to be transferred to punch 1310. Rotational motion generated by electric motor 1311 may be converted to another variety of motion, such as, for instance, reciprocating motion. Such reciprocating motion may be effected using a crank mechanism 1312. The reciprocating motion may be then converted to an oscillating motion using a rack and pinion gear assembly 1325 also shown in FIG. 12 in more detail. An oscillating rack and pinion gear assembly 1325 may be coupled to another gear with an internal spline 1313. A spline shaft 1314 may be gear-coupled to internal spline 1313. Spline shaft 1314 may be extended to an output shaft 1315. However, this is merely an example of a method of translating rotational motion to oscillatory motion and then translating that motion to a punch using a mechanized system. As mentioned in FIG. 11a there are a variety of methods of translating motion through a device and claimed subject matter is not limited in this regard. According to a particular embodiment, output shaft 1315 may have a depth stop collar 1316 and may pass through a depth adjusting nut 1317. Depth adjusting nut 1317 may be threaded to bearing block 1318 and may be moved in the axial direction limiting the axial travel of depth stop collar 1316. A return spring (not shown) may be housed in bearing block 1318 and may work against a depth stop collar 1316 on output shaft 1315. A punch holder 1319 may pass through hollow screw shaft 1320 and bearing block 1318 and may be coupled to output shaft 1315. A hollow screw shaft 1320 that supports punch holder 1319 may be threaded on to bearing block 1318 and fixed in position by means of a counter nut 1321. A trigger 1321 with a fork 1322 on one end may be operated manually and acts on depth stop collar 1316 to move the oscillating or rotating punch 1310 forward against a return spring (not shown). Trigger 1321 may be released enabling return spring (not shown) to reset punch 1310 back to the original position. While performing a follicular dissection procedure, a user may align punch 1310 to a hair and touch the skin surface with punch 1310. In a particular embodiment, a user may activate oscillation punch 1310 using punch switch 1323. Additionally, trigger 1321 may be pulled enabling punch 1310 to extend, while oscillating, with punch holder 1319 until stopped by depth stop collar 1316. Trigger 1321 may be release retracting punch 1310. The rate of punch advance may be controlled by the user and may be based on the individual conditions of the skin. As mentioned above, punch 1310 oscillation may be about 30 to 30,000 strokes per minute. However, this is merely an example of a method controlling the motion of a punch coupled to a PFID and claimed subject matter is not limited in this regard.

Figure 14:
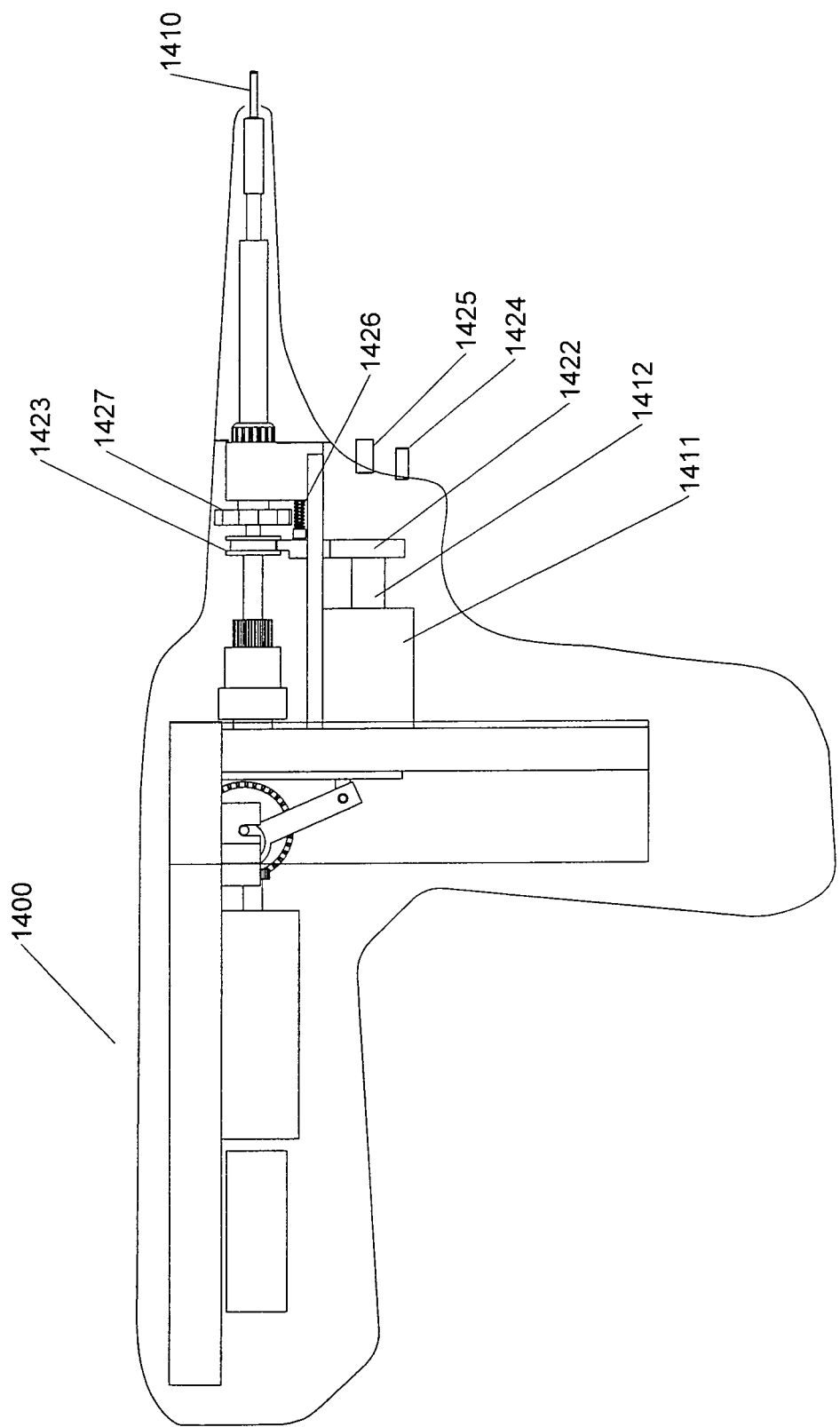
FIG. 14 is a diagram showing Powered Follicular Isolation Device comprising a solenoid actuated punch translation mechanism according to an embodiment.

FIG. 14 illustrates a particular embodiment of a punch 1410 coupled to a PFID 1400 comprising a solenoid actuated punch translation mechanism. This embodiment is similar to that depicted in FIG. 13; however, in this embodiment punch advancing motion may be performed by means of a linear solenoid 1411. Solenoid actuator 1412 of a linear solenoid 1411 may be connected to a fork 1422 that acts on depth stop collar 1423 to prevent insertion of punch 1410 beyond a desired depth into the skin of a patient during a follicular dissection procedure. Oscillation switch 1424 may be activated. Punch 1410 may oscillate in response to activation of oscillation switch 1424. Punch advancing switch 1425 may be activated causing a solenoid actuator 1412 to be extended from solenoid 1411. This action may extend punch 1410 forward. Punch 1410 may oscillate and may be extended into the skin of a patient during a follicular dissection procedure until depth stop collar 1423 is stopped by depth adjusting nut 1427. Punch advancing switch 1425 may be released enabling a return spring 1426 to push back on punch 1410 retracting punch 1410. Punch 1410 oscillating motion may be 60 to 30,000 strokes per min. A linear solenoid 1411 may enable a fast rate of punch advance. Additionally, solenoid actuator 1412 acting time or time it takes to extend and/or retract punch may be adjusted from about 200 millisecond (ms) to 1 second. In another embodiment, two actuators may be coupled together mechanically and electronically (not shown) to give a scoring and a dissecting movement one after the other. It should be understood that the foregoing is merely an example of a method of transferring and converting rotational motion from PFID 1400 to a punch using a mechanized system and of controlling the depth of a punch. As mentioned in FIG. 11 there are a variety of methods of translating motion through a device and claimed subject matter is not limited in this regard.

Figure 15:
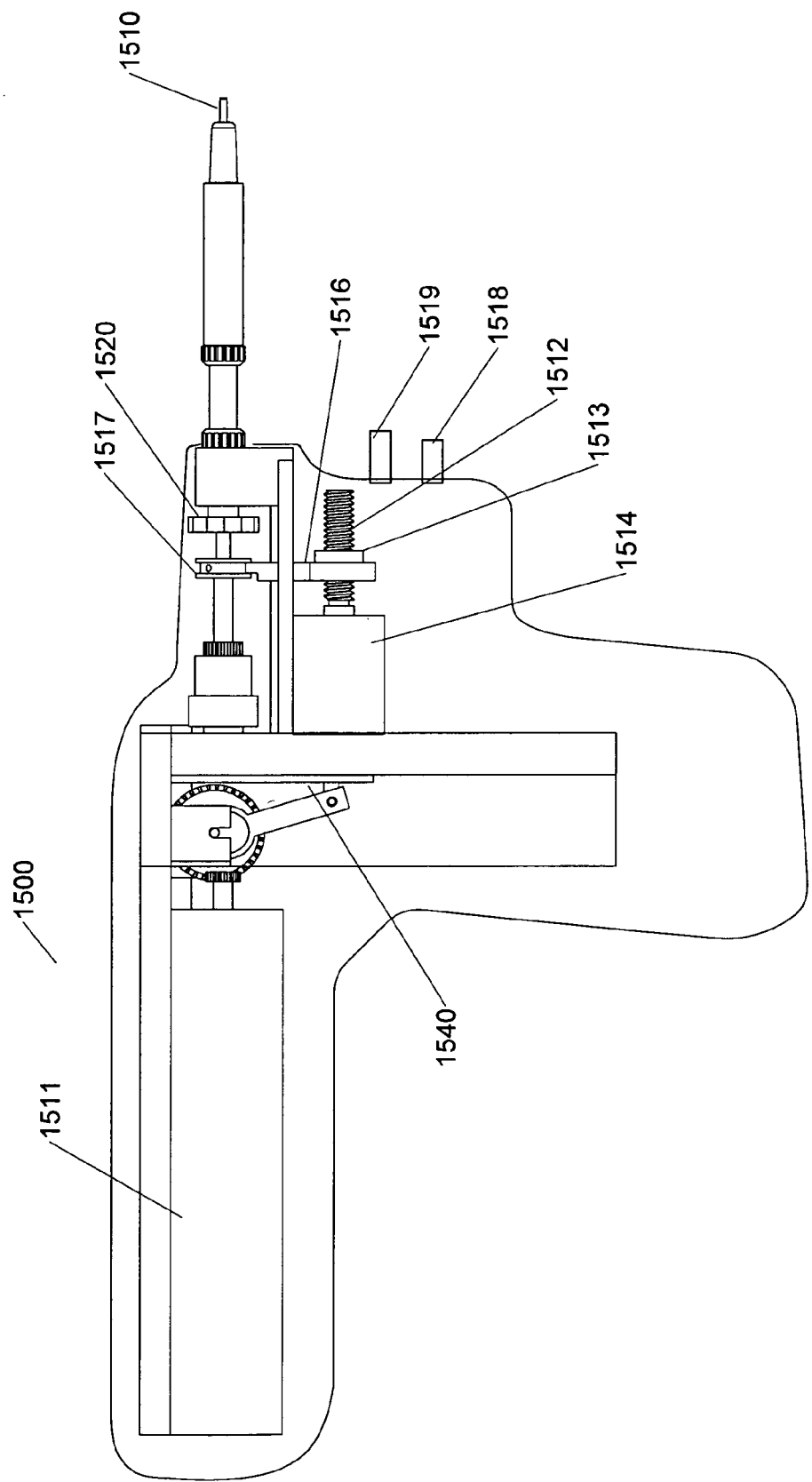
FIG. 15 is a diagram showing Powered Follicular Isolation Device comprising a motorized lead screw punch translation mechanism according to an embodiment.

FIG. 15 illustrates another embodiment of a punch 1510 coupled to a PFID 1500 comprising a motorized lead screw punch translation mechanism. This embodiment may be similar to that shown in FIG. 13, however, punch 1510 advance mechanism may be somewhat different. In a particular embodiment, punch 1510 may oscillate and also extend and retract when needed. An electric motor 1511 may generate rotational motion which may be converted to a reciprocating motion using a crank mechanism as described in detail FIG. 12. Reciprocating motion may be converted to an oscillating motion using a rack and pinion 1540 gear assembly also described in FIG. 12 above. In a particular embodiment, punch 1510 advance may be performed by means of a lead screw 1512 and nut 1513 assembly with a second electric motor 1514. Second electric motor 1514 may drive lead screw 1512 in either a clockwise or counterclockwise direction. Nut 1513 assembled on lead screw 1512 by threading may move linearly on lead screw 1512 back and forth depending on the direction of rotation of the motor. Nut 1513 may be connected to a fork 1516 that may act on depth stop collar 1517. When a user aligns punch 1510 to a hair and touches the skin surface, punch oscillate switch 1518 may be activated enabling punch 1510 to oscillate. Punch advancing switch 1519 may also be activated enabling second electric motor 1514 to rotate lead screw 1512 and in turn move nut 1513 and fork 1516 forward at a constant rate. Punch 1510 may thus be inserted into the skin of a patient during a follicular dissection procedure until depth stop collar 1517 comes into contact with and activates an electrical switch (not shown) mounted on depth adjust nut 1520. Switch (not shown) may stop second electric motor 1514 and/or may reverse the direction of rotation of lead screw 1512. As a result, punch 1510 may be retracted backwards to an original position. Switch 1519 may be released stopping electric motor 1514. The axial motion of punch 1510 extension and/or retraction may be performed at a constant rate and/or the rate may be changed by changing electromotor speed or by using a lead screw 1512 and nut 1513 assembly with a different thread pitch. Punch 1510 advance rate may be about 1 mm to 2,500 mm per minute. Punch 1510 oscillation included angles from 5 to 360 degrees. Punch 1510 oscillation rate may be about 30 to 30,000 strokes per minute. The oscillation angle, oscillation rate and punch 1510 advance rate can also be higher or lower than the indicated values. It should be understood that the foregoing is merely an example of a method of transferring motion from PFID 1500 to a punch using a mechanized system and of controlling the depth of a punch. As mentioned in FIG. 11 there are a variety of methods of translating motion through a device and claimed subject matter is not limited in this regard.

Figure 16:
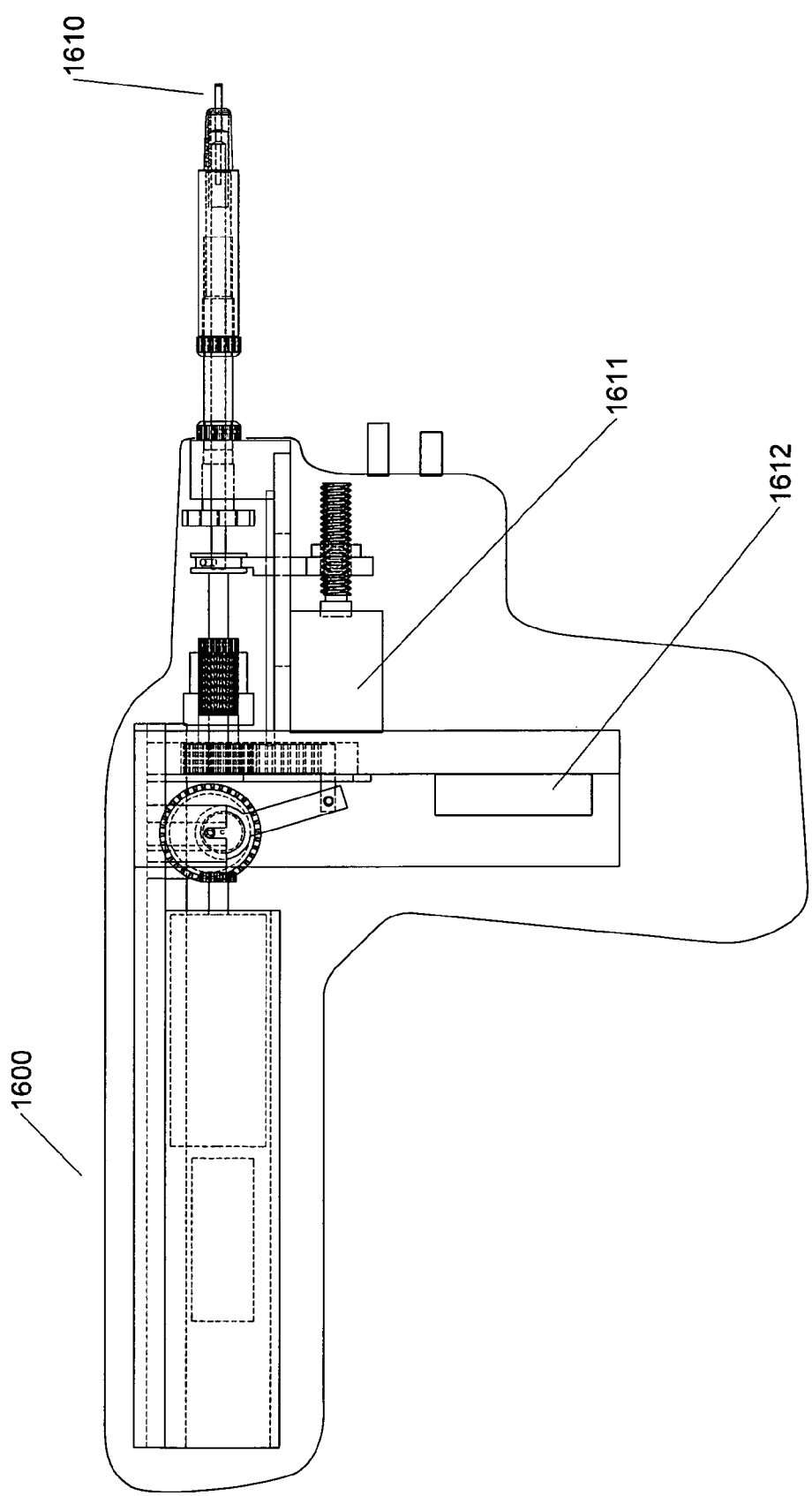
FIG. 16 is a diagram showing Powered Follicular Isolation Device comprising programmable punch translation mechanism according to an embodiment.

FIG. 16 illustrates a particular embodiment of a punch 1610 coupled to a PFID 1600 comprising a controllable and programmable punch translation mechanism. A PFID 1600 may comprise a controllable and programmable punch translation mechanism in which number, rate and sequence of punch advance and retract motions are controllable and programmable. Such a drive may involve a step motor 1611 and an electronic programmable controller 1612. In a particular embodiment, punch advance may take place in a number of steps where a punch 1610 in motion moves forward with respect to PFID 1600 a particular distance and moves back to a reference position. On a second extension punch 1610 may move further forward and move back to a reference position. For example, a rotating or oscillating punch may contact the skin which would be a reference or zero position. When the punch advance is actuated, the punch may be inserted into the skin 0.5 mm, and then may move back to a reference position. Next, punch 1610 may move deeper into the skin, such as a depth of 2 mm, and then may move back to a reference position, and again may move deeper into the skin, such as a depth of 4 mm and then move back to a reference position. The rate of punch advance may be about 30 to 100,000 mm/min and the punch retraction rate may be 30 to 100,000 mm/min. The number of steps, the sequence and the rate of advance may be adjusted to any desired values. A stepper motor controller/driver 1612 may work in a stand alone mode or may be interfaced with a PC (not shown). When interfaced with a PC, the motion control commands may be given from the PC. A stand-alone stepper motor control system may be hand held and packaged with a driver and/or power supply. The controller 1612 may be preprogrammed and the motion programs can be initiated from various types of operator interfaces, such as a keypad or switch, or through an auxiliary input-output device.

While certain features of claimed subject matter have been illustrated as described herein, many modifications, substitutions, changes and equivalents will now occur to those skilled in the art. It is, therefore, to be understood that the claims are intended to cover all such embodiments and changes as fall within the true spirit of claimed subject matter.

What is claimed is:
1. An apparatus comprising:
a cylindrical punch, comprising an approximately cylindrical housing and at least two members forming an approximately cylindrical shape, the at least two members of the cylindrical punch having inclined surfaces and forming a first end and a second end, the second end having an edge comprising at least three denticulations, at least a portion of the second end comprising the edge extending in an approximately axial direction out of the approximately cylindrical housing to perform a hair follicle dissection, at least a portion of an outer surface of the at least two members abutting an inner surface of the approximately cylindrical housing, at least a portion of the second end formed by the at least two members having an approximately uniform diameter larger than a diameter of the approximately cylindrical housing; wherein
the edge forms an approximately circular shape;
at least one of the at least three denticulations comprises at least first, second, and third cutting surfaces, the first cutting surface being disposed on the edge of the cylindrical punch,
the cylindrical punch to be rotatable around a longitudinal axis projected through the first end and the second end, and
the approximately uniform diameter of the second end being formed by the at least two members and being adjustable to two or more different fixed sizes while maintaining an approximately circular shape in response to axial movement of the inclined surfaces of the at least two members relative to the approximately cylindrical housing.

2. The apparatus of claim 1 wherein at least one of the at least three denticulations is sharp.

3. The apparatus of claim 1 wherein at least one of the at least three denticulations further comprises a shape comprising a scallop, square, semicircle, or polygon.

4. The apparatus of claim 1, the apparatus to dissect tissue.

5. The apparatus of claim 1 and further comprising a motion conversion mechanism coupled to the cylindrical punch.

6. The apparatus of claim 1, wherein the first cutting surface comprises one or more approximately arced shapes.

7. The apparatus of claim 1, wherein the first cutting surface comprises one or more sharp points.

8. The apparatus of claim 7, wherein the one or more sharp points comprise points at which portions of the second and third cutting surfaces meet at the edge of the second end.

9. The apparatus of claim 1, wherein the second or third cutting surfaces comprise one or more approximately arced shapes.

10. The apparatus of claim 1, wherein at least a majority of the at least three denticulations are capable of cutting skin tissue approximately simultaneously during operation of the cylindrical punch.

* * * * *